US007713981B2

(12) United States Patent
Zervos

(10) Patent No.: US 7,713,981 B2
(45) Date of Patent: *May 11, 2010

(54) METHOD AND COMPOUNDS FOR INHIBITION OF CELL DEATH

(75) Inventor: Antonis Zervos, Oviedo, FL (US)

(73) Assignee: University of Central Florida, Orlando, FL (US)

( * ) Notice: Subject to any disclaimer, the term of this patent is extended or adjusted under 35 U.S.C. 154(b) by 966 days.

This patent is subject to a terminal disclaimer.

(21) Appl. No.: 10/728,056

(22) Filed: Dec. 4, 2003

(65) Prior Publication Data

US 2004/0171629 A1 Sep. 2, 2004

Related U.S. Application Data

(63) Continuation-in-part of application No. 10/369,311, filed on Feb. 20, 2003.

(60) Provisional application No. 60/361,902, filed on Feb. 28, 2002.

(51) Int. Cl.
*A01N 43/54* (2006.01)
*C07D 239/42* (2006.01)
*C07D 401/04* (2006.01)
*C07D 239/00* (2006.01)
*C07D 239/70* (2006.01)
*C07D 471/00* (2006.01)
*C07D 487/00* (2006.01)
*C07D 239/02* (2006.01)

(52) U.S. Cl. ............... 514/256; 544/245; 544/299; 544/304

(58) Field of Classification Search ............ 514/256, 514/879; 544/245, 299, 304
See application file for complete search history.

(56) References Cited

U.S. PATENT DOCUMENTS

| 6,004,794 A | 12/1999 | Karran et al. |
| 6,245,773 B1 | 6/2001 | Wong et al. |
| 2002/0010186 A1 | 1/2002 | Wong et al. |
| 2003/0073629 A1 | 4/2003 | Alnemri |
| 2005/0042213 A1* | 2/2005 | Gelder et al. ............ 424/94.64 |

OTHER PUBLICATIONS

M. Daemen et al. "Inhibition of apoptosis induced by ischemia-reperfusion prevents inflammation," The Journal of Clinical Investigation, vol. 104, No. 5, pp. 541-549, Sep. 1999.
B. Van Der Water et al. "Cleavage of the actin-capping protein α-adducin at asp-asp-ser-asp$^{633}$-ala by caspase-3 is preceded by its phosphorylation on serine 726 in cisplatin-induced apoptosis of renal epithelial cells," The Journal of Biological Chemistry, vol. 275, No. 33, pp. 25805-25813, Aug. 18, 2000.
G. Kaushal et al. "Role and regulation of activation of caspases in cisplatin-induced injury to renal tubular epithelial cells," Kidney International, vol. 60, pp. 1726-1736, 2001.
M. Daemen et al. "Activated caspase-1 is not a central mediator of inflammation in the course of ischemia-repurfusion," Transplantation, vol. 71, No. 6, pp. 778-784, Mar. 27, 2001.
L. Faccio et al. "Characterization of a novel human serine protease that has extensive homology to a bacterial heat shock endoprotease HtrA and is regulated by kidney ischemia," The Journal of Biological Chemistry, vol. 275, No. 4, pp. 2581-2588, Jan. 28, 2000.
J. Jones et al., "Loss of Omi Mitochondrial Protease activity causes the neuromuscular disorder of mnd2 mutant mice," Nature, vol. 425 (6959), pp. 721-727, Oct. 2003.
L. Cilenti et al. "Characterization of a novel and specific inhibitor for the pro-apoptotic protease Omi/HtrA2," The Journal of Biological Chemistry, vol. 278, No. 13, pp. 11489-11494, Mar. 28, 2003.
R. Hegde et al. "Identification of Omi/HtrA2 as a mitochondrial apoptotic serine protease that disrupts inhibitor of apoptosis protein-caspase interaction," The Journal of Biological Chemistry, vol. 277, No. 1, pp. 432-438, Jan. 4, 2002.
Cilenti, L. et al., "Characterization of a Novel and Specific Inhibitor for the Pro-Apoptotic Protease Oml/HtrA2", *The Journal of Biological Chemistry*, v. 278, pp. 11489-11494, 2003.

* cited by examiner

*Primary Examiner*—Sreeni Padmanabhan
*Assistant Examiner*—Kendra D Carter
(74) *Attorney, Agent, or Firm*—Thomas J. Engellenner; George A. Xixis; Nutter McClennen & Fish LLP

(57) ABSTRACT

The invention is directed to methods and compositions for inhibiting caspase-independent apoptosis. In particular, methods and compositions for inhibiting Omi/HtrA2 activity, as well as method for identifying other inhibitors of Omi/HtrA2. Also disclosed are Omi/HtrA2 specific substrates and methods for identifying other substrates of Omi/HtrA2.

12 Claims, 10 Drawing Sheets ucf-103 ucf-104

SEQUENCE LISTING

<160> NUMBER OF SEQ ID NOS: 7

<210> SEQ ID NO 1
<211> LENGTH: 9
<212> TYPE: PRT
<213> ORGANISM: Homo sapiens
<220> FEATURE:

-continued

```
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 1

Pro Arg Ala Ala Xaa Xaa Thr Xaa Xaa
1               5

<210> SEQ ID NO 2
<211> LENGTH: 52
<212> TYPE: DNA
<213> ORGANISM: Murinae gen. sp.

<400> SEQUENCE: 2
tcgaattcgc tgggggagga gacagtactg tctcctcccc cagcgaattt tt         52

<210> SEQ ID NO 3
<211> LENGTH: 53
<212> TYPE: DNA
<213> ORGANISM: Murinae gen. sp.

<400> SEQUENCE: 3
taagcgaccc cctcctctgt catgacagag gaggggtcg cttaaaaatc tag         53

<210> SEQ ID NO 4
<211> LENGTH: 18
<212> TYPE: DNA
<213> ORGANISM: Murinae gen. sp.

<400> SEQUENCE: 4
gcggggcggg gtgcaaac                                               18

<210> SEQ ID NO 5
<211> LENGTH: 17
<212> TYPE: DNA
<213> ORGANISM: Murinae gen. sp.

<400> SEQUENCE: 5
gacagccagc accgtgg                                                17

<210> SEQ ID NO 6
<211> LENGTH: 17
<212> TYPE: DNA
<213> ORGANISM: Murinae gen. sp.

<400> SEQUENCE: 6
ttcgttgccg gtccaca                                                17

<210> SEQ ID NO 7
<211> LENGTH: 18
<212> TYPE: DNA
<213> ORGANISM: Murinae gen. sp.

<400> SEQUENCE: 7
accagcgcag cgatatcg                                               18
```

METHOD AND COMPOUNDS FOR INHIBITION OF CELL DEATH

RELATED CASE INFORMATION

This is Continuation-In-Part application that claims priority to U.S. Provisional Patent Application No. 60/361,902, filed Feb. 28, 2002, and U.S. Utility patent application Ser. No. 10/369,311, filed Feb. 20, 2003, which are incorporated herein by their entirety.

BACKGROUND OF THE INVENTION

The technical field of this invention relates generally to alteration of apoptosis in a cell and modification of pathways involved in apoptosis including the treatment of diseases that involve apoptotic pathways. In particular, the invention pertains to a class of inhibitors that inhibit mitochondrial homeostasis, caspase-dependent, and caspase-independent apoptosis by affecting Omi/HtrA2 activity.

Apoptosis, which is also referred to as programmed cell death, is a form of cell death characterized by membrane blebbing and nuclear DNA fragmentation. Apoptotic cell death is morphologically distinct from necrotic cell death and is important in the normal development and maintenance of multicellular organisms.

Since apoptosis functions in maintaining tissue homeostasis in a range of physiological processes such as embryonic development, immune cell regulation and normal cellular turnover, the dysfunction or loss of regulated apoptosis can lead to a variety of pathological disease states. For example, the loss of apoptosis can lead to the pathological accumulation of self-reactive lymphocytes that occurs with many autoimmune diseases. Inappropriate loss or inhibition of apoptosis can also lead to the accumulation of virally infected cells and of hyperproliferative cells such as neoplastic or tumor cells. Similarly, the inappropriate activation of apoptosis can also contribute to a variety of pathological disease states including, for example, acquired immunodeficiency syndrome (AIDS), neurodegenerative diseases and ischemic injury. Treatments that are specifically designed to modulate the apoptotic pathways in these and other pathological conditions can alter the natural progression of many of these diseases.

Although apoptosis is mediated by diverse signals and complex interactions of cellular gene products, the results of these interactions ultimately feed into a cell death pathway that is evolutionarily conserved between humans and invertebrates. The pathway, itself, is a cascade of proteolytic events analogous to that of the blood coagulation cascade.

Several gene families and products that modulate the apoptotic process have now been identified. Key to the apoptotic program is a family of cysteine proteases termed caspases. The human caspase family includes Ced-3, human ICE (interleukin-1-beta converting enzyme) (caspase-1), ICH-1 (caspase-2), CPP32 (caspase-3), $ICE_{reIII}$ (caspase-4), $ICE_{reIII}$ (caspase-5), Mch2 (caspase-6), ICE-LAP3 (caspase-7), Mch5 (caspase-8), ICE-LAP6 (caspase-9), Mch4 (caspase-10), caspase 11-14, and others. Capsases can be positioned as downstream effectors of apoptosis.

The serine protease Omi, is also involved in apoptosis. Omi (also known as "HtrA2" and "Omi/HtrA2") was identified as a mitochondrial direct inhibitor of apoptosis protein (IAP) binding protein, and is released from the mitochondria upon induction of apoptosis by apoptotic stimuli (Hegde et al. (2002) *J Biol. Chem.*, 277: 432-438). The mature Omi/HtrA2 protein contains a conserved IAP-binding motif that comprises the tetra peptide motif "AVPS" at its N terminus. It has been demonstrated that the deregulated expression of Omi/HtrA2 in the cytoplasm of mammalian cells induces apoptosis in these cells, indicating that Omi/HtrA2 could participate in the mitochondrial apoptotic pathway.

Mature Omi/HtrA2 is released from the mitochondria into the cytosol upon disruption of the outer mitochondrial membrane during apoptosis. Mature Omi/HtrA2 can induce apoptosis in human cells in a caspase-independent manner through its protease activity and in a caspase-dependent manner via its ability to disrupt caspase-IAP interaction.

Since Omi/HtrA2 is present in all mammalian cells and by its activity of disrupting the inhibition of the "apoptosis protein-caspase interaction" decreases the cell lifetime, it would be important to discover an inhibitor of the adverse activity of Omi/HtrA2 and homologous proteins.

Accordingly, it would be useful to identify a class of inhibitors that inhibit Omi/HtrA2. A need also exists to determine the peptides involved in the caspase-independent pathway of apoptosis such as substrates of Omi/HtrA2, as well as methods and compositions that inhibit such pathways. It would also be useful to find ways to use these methods and compositions to prevent, reduce or ameliorate a disorder associated with apoptosis.

SUMMARY OF THE INVENTION

The invention is based on the discovery that the activity of Omi/HtrA2 can be inhibited by a class of compounds referred to as "apoptosis inhibiting compounds." The mature serine protease Omi/HtrA2 was identified as a mitochondrial direct baculoviral inhibitor of apoptosis protein repeat3 (BIR3)-binding protein and a caspase activator (Hegde et al. (2002) *J Biol. Chem.*, 277: 432-438). The involvement of a mitochondrial serine protease in the apoptotic pathway emphasizes the role of the mitochondria in cell death. Therefore, the identification and use of apoptosis. These apoptotic inhibiting compounds can be formulated into pharmaceutical compositions. The methods and compositions of the invention can be used to inhibit mitochondrial homeostasis, caspase-dependent, and caspase-independent apoptosis by affecting Omi/HtrA2 activity.

Accordingly, in one aspect the invention pertains to a pharmaceutical composition for inhibiting cellular apoptosis, the composition comprising at least one apoptosis inhibiting compound that can modulate caspase-independent apoptosis.

The pharmaceutical composition can further comprise a pharmaceutical acceptable excipient. In one embodiment, the apoptosis inhibiting compound, comprise the general structure shown in FIG. 1a, where $R_1$ is selected from the group consisting of a nitro group, a carboxy group, a hydroxide, an aliphatic group, an aromatic group, an acyl group, an alkoxy group, an alkylene group, an alkenylene group, an alkynylene group, a hydroxycarbonylalkyl group, an anhydride, an amide, an amine, and a heterocyclic aromatic group. In a preferred embodiment, the apoptosis inhibiting compound has the structure shown in FIG. 1b. In another embodiment, the apoptosis inhibiting compound comprises the general structure shown in FIG. 2a where $R_1$ is selected from the group consisting of a nitro group, a carboxy group, a hydroxide, an aliphatic group, an aromatic group, an acyl group, an alkoxy group, an alkylene group, an alkenylene group, an alkynylene group, a hydroxycarbonylalkyl group, an anhydride, an amide, an amine, and a heterocyclic aromatic group. In a preferred embodiment, the apoptosis inhibiting compound has the structure shown in FIG. 2b. In yet another embodiment, the apoptosis inhibiting compound comprises the general structure shown in FIG. 3a, where $R_1$ is selected from the group consisting of a nitro group, a carboxy group, a hydroxide, an aliphatic group, an aromatic group, an acyl group, an alkoxy group, an alkylene group, an alkenylene group, an alkynylene group, a hydroxycarbonylalkyl group, an anhydride, an amide, an amine, and a heterocyclic aromatic group. In a preferred embodiment, the apoptosis inhibiting compound has the structure shown in FIG. 3b. In yet another embodiment, the apoptosis inhibiting compound comprises the general structure shown in FIG. 4a, where $R_1$ is selected from the group consisting of a nitro group, a carboxy group, a hydroxide, an aliphatic group, an aromatic group, an acyl group, an alkoxy group, an alkylene group, an alkenylene group, an alkynylene group, a hydroxycarbonylalkyl group, an anhydride, an amide, an amine, and a heterocyclic aromatic group. In a preferred embodiment, the apoptosis inhibiting compound has the structure shown in FIG. 4b.

The pharmaceutical composition may also comprise a mixture of apoptosis inhibiting compounds as long as the apoptosis inhibiting compounds in the mixture can modulate caspase-independent apoptosis. For example, the composition may have any combinations of the compounds shown in FIGS. 1-4.

In another aspect, the invention pertains to a method for inhibiting caspase-independent apoptosis in a cell by contacting a cell having Omi/HtrA2 activity with at least one apoptosis inhibiting compound, such that the apoptosis inhibiting compound interacts with Omi/HtrA2 to inhibit the activity of Omi/HtrA2, wherein the inhibition of Omi/HtrA2 activity reduces apoptosis in the cell; and monitoring the inhibition of apoptosis. The inhibiting compound can selected from the group consisting of the structure shown in FIG. 1a, FIG. 2a, FIG. 3a and FIG. 4a. Preferably, the apoptosis inhibiting compound has the structure shown in FIG. 1b, FIG. 2b, FIG. 3b, and FIG. 4b.

In yet another aspect, the invention pertains to a method of inhibiting Omi/HtrA2 activity, comprising contacting a cell having Omi/HtrA2 activity with an apoptosis inhibiting compound; and monitoring the inhibition of Omi/HtrA2 activity. The cell to be contacted can either be an in vitro cell or an in vivo cell. The apoptosis inhibiting compound can be anyone of the aforementioned inhibitors. The step of monitoring Omi/HtrA2 activity can be by monitoring a change in fluorescene of an Omi/HtrA2 substrate coupled to a fluorescent marker, or by monitoring the inhibition of Omi/HtrA2 activity further comprises monitoring apoptosis of the cell.

In yet another aspect, the invention pertains to a method for modifying a disorder associated with caspase-independent apoptosis comprising administering a therapeutically effective amount of a composition comprising at least one apoptosis inhibiting compound such that the apoptosis inhibiting compound interacts with Omi/HtrA2 to inhibit the activity of Omi/HtrA2, wherein the inhibition of Omi/HtrA2 activity reduces apoptosis in the cell; and monitoring the amelioration of the disorder by measuring the change in caspase-independent apoptosis. The disorder can be selected from the group consisting of kidney failure, heart failure, heart attack, stroke, neurodegenerative disease, cancers and tumors. In a preferred embodiment, the disorder is kidney failure.

In yet another aspect, the invention pertains to a method of preventing tubular cell death, comprising administering an apoptosis inhibiting compound, wherein the apoptosis inhibiting compound interacts with Omi/HtrA2 such that the apoptosis inhibiting compound interacts with Omi/HtrA2 to inhibit the activity of Omi/HtrA2, wherein the inhibition of Omi/HtrA2 activity prevents tubular cell death; and monitoring the prevention of tubular cell death. The tubular cell death can be associated with the proximal tubules of the kidney, and may cause renal apoptosis and/or renal ischeamia.

In yet another aspect, the invention pertains to a method for identifying a substrate associated with caspase-independent apoptosis, comprising contacting a cell extract with recombinant Omi/HtrA2, wherein the recombinant Omi/HtrA2 has proteolytic activity. The results from the contacted cell extract can be compared with the results of the with a control sample that has not been incubated with recombinant Omi/HtrA2. A substrate associated with caspase-independent apoptosis can be identified by monitoring a change in the electophoretic mobility of a protein in the cell extract incubated with recombinant Omi/HtrA2, such that a change in electophoretic mobility of the protein indicates that the protein is a substrate of Omi/HtrA2. The change in electophoretic mobility can be the disappearance of a protein in the cell extract incubated with recombinant Omi/HtrA2. In one embodiment, the protein associated with caspase-independent apoptosis is obtained from a kidney cell extract. Preferably, the protein associated with caspase-independent apoptosis is a substrate for Omi/HtrA2. In one embodiment, the substrate associated with caspase-independent apoptosis is 14-3-3. In another embodiment, the substrate associated with caspase-independent apoptosis is Annexin V.

In yet another embodiment, the invention pertains to a method for identifying a compound that inhibits caspase-independent apoptosis, comprising contacting the candidate compound with a substrate coupled to a fluorescent marker in the presence of recombinant Omi/HtrA2, wherein the recombinant Omi/HtrA2 has proteolytic activity against the substrate, and monitoring the change in fluorescence, whereby a candidate compound is identified as being an inhibitor of caspase-independent apoptosis if the candidate compound inhibits or blocks the proteolytic activity of recombinant Omi/HtrA2. The substrate can be a specific Omi/HtrA2 substrate selected from the group consisting of 14-3-3 and annexin V. Alternatively, the substrate can be a general substrate such as casein. The fluorescent marker can be selected from the group consisting of fluorescein isothiocyanate (FITC), cyanine dye-5 (CY5), cyanine dye-3 (Cy3), cyanine dye-7 (Cy7), allophycocyanin (APC), tetramethyl rhodamine isothiocyanate (TRITC), and phycoerythrin (PE). Preferably, the fluorescent marker is FITC. The recombinant Omi/HtrA2 is MBP-Omi$_{134-458}$

BRIEF DESCRIPTION OF FIGURES

FIG. 11a is a photograph of Western blot showing that the protein levels of Omi/HtrA2 increases in MPT cells induced with various cisplatin and antimycin apoptotic stimuli, while

DETAILED DESCRIPTION

Figure 1A:
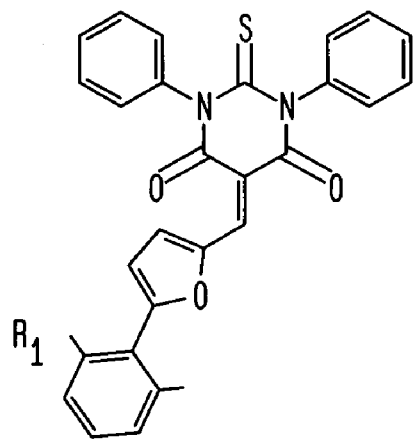
FIG. 1a is the general structure of an apoptosis inhibiting compound.

The practice of the present invention employs, unless otherwise indicated, conventional methods of virology, microbiology, molecular biology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.))

So that the invention is more clearly understood, the following terms are defined:

The term "apoptosis" as used herein refers to the art recognized use of the term for an active process of programmed cell death characterized by morphological changes in the cell. Apoptosis is characterized by membrane blebbing and nuclear DNA fragmentation. Apoptosis can occur via two pathways, the caspase-dependent pathway, where involves caspases where Omi/HtrA2 interacts with an inhibitor of apoptosis protein (IAP) and activates the caspase pathway. Alternatively, apoptosis can occur via the caspase-independent pathway, where Omi/HtrA2 acts as a serine protease and does not involve caspases.

The phrase "inhibitor of apoptosis protein (IAP)" as used herein refers to the art recognized use of the phrase for a protein that contains at least one copy of Baculovirus IAP of a repeat (BIR) domain and suppresses apoptosis when overexpressed and is known to bind and inhibit caspases.

The term "zymogen" as used herein refers to the inactive proform of an enzyme e.g. a caspase, which is typically activated by proteolysis.

The term "caspase" as used herein refers to a cysteine protease that specifically cleaves proteins after Asp residues. Caspases are initially expressed as zymogens, in which a large subunit is N-terminal to a small subunit. Caspases are generally activated by cleavage at internal Asp residues. Caspases are found in a myriad of organisms, including human, mouse, insect (e.g., *Drosophila*), and other invertebrates (e.g., *C. elegans*). The caspases include, but are not limited to, Caspase-1 (also known as "ICE"), Caspase-2 (also known as "ICH-1"), Caspase-3 (also known as "CPP32," "Yama," "apopain"), Caspase-4 (also known as "ICE$_{reIII}$"; "TX," "ICH-2"), Caspase-5 (also known as "ICE$_{reIII}$"; "TY"), Caspase-6 (also known as "Mch2"), Caspase-7 (also known as "Mch3," "ICE-LAP3" "CMH-1"), Caspase-8 (also known as "FLICE;" "MACH;" "Mch5"), Caspase-9 (also known as "ICE-LAP6;" "Mch6"), Caspase-10 (also known as "Mch4," "FLICE-2").

The phrase "caspase-dependent apoptosis" as used herein refers to an apoptosis pathway that involves caspases. In a caspase-dependent apoptosis pathway, mature Omi/HtrA2 comprising the tetrapeptide motif "AVPS" which binds to x-chromosome linked Inhibitor of Apoptosis Protein (XIAP), and causes caspase activation, which results in apoptosis.

The phrase "caspase-independent apoptosis" as used herein refers to apoptosis pathway that does not involves caspases. Instead, Omi/HtrA2 behaves like a serine protease exhibiting proteolytic activity. When Omi/HtrA2 functions as a protease, it proteolytically cleaves specific protein substrates leading to apoptosis.

Figure 1B:
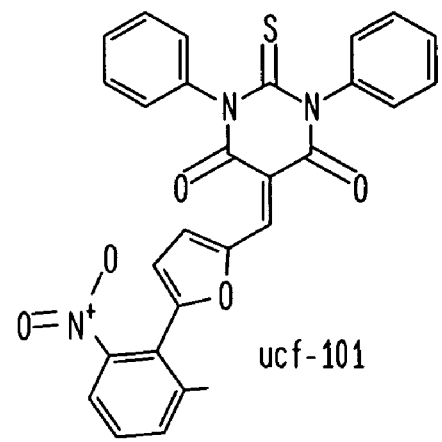
FIG. 1b is the specific structure of Ucf 101.

The term "apoptosis inhibiting compound" as used herein refers to an agent that can reduce apoptosis by a detectable amount by acting on a pathway involved in apoptosis. The agent can act by inhibiting or blocking a particular step in the apoptotic pathway, for example by blocking or inhibiting the activity of protein involved in the pathway, such as inhibiting the activity of Omi/HtrA2. The apoptotic pathway includes both caspase-dependent apoptosis, as well as caspase-independent apoptosis. In a preferred embodiment, the apoptosis inhibiting compound acts on the caspase-independent apoptosis pathway to reduce or inhibit apoptosis by a detectable amount. Examples of apoptosis inhibiting compounds, include, but are not limited to those structures shown in FIG. 1a, FIG. 2a, FIG. 3a, and FIG. 4a. Preferred apoptosis inhibiting compounds are referred to as "Ucf-101" (shown in FIG. 1b), "Ucf-102" (shown in FIG. 2b), "Ucf-103" (shown in FIG. 3b) and "Ucf 104" (shown in FIG. 4b). A particularly preferable apoptosis inhibiting compound is Ucf 101. Also within the scope of the invention are the use of combinations and mixtures of apoptosis inhibiting compounds, for example, a mixture comprising Ucf-101 and Ucf-102; Ucf-101, Ucf-102, and Ucf-103; or Ucf-101, Ucf-102, Ucf-103 and Ucf 104, or any combinations thereof.

The term "inhibit" or "inhibiting" as used herein refers to a measurable reduction of apoptotic activity. Preferably a reduction of activity of at least about 20%. More preferably the reduction of activity is about 30%, 40%, 50%, 60%, 80%, 90% and even more preferably, about 100%.

The term "modulate" or "modify" are used interchangeably herein and refer to an alleviation of at least one target protein or gene involved in the caspase-independent pathway for apoptosis. Such that apoptosis is inhibited or reduced. A target protein can be for example, Omi/Htr2A. Modification of the Omi/Htr2A may occur when an apoptosis inhibiting compound interacts with Omi/Htr2A an alters the functional activity of Omi/Htr2A. A modification in apoptosis can be assessed by monitoring cell blebbing DNA fragmentation, and the like.

The phrase "a disorder associated with Omi/Htr2A activty" or "a disease associated with Omi/Htr2A activity" as used herein refers to any disease state associated with the expression of Omi/Htr2A. Examples include but are not limited to kidney failure, ischemia-reperfusion injury, heart failure, neurodegeneration disorders such as Alzheimer's disease, Parkinson's disease, Huntington's disease and amytrophic lateral sclerosis; inflammation; osteoarthritis; human immunodeficiency virus); bacterial infection, cell proliferative disorders, cancers, and diabetes.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The invention is described in more detail in the following sections:

I. Apoptosis and Omi/HtrA2

In one aspect, the invention pertains to reducing, inhibiting, preventing or altering apoptosis, particularly caspase-independent apoptosis. Apoptosis or programmed cell death was originally described by Kerr et al., in 1972 (Kerr, et al. (1972) *Br J Cancer*, 26, 239-57), as a new cell-autonomous mechanism of death aimed at removing damaged, mutated or aged cells. Mitochondria, are directly linked to the process of apoptosis to the extent that they are now termed "killer organelles" (Ravagnan, et al. (2002) *J Cell Physiol*, 192, 131-7). Mitochondria contain several proteins in their inter-membrane space which are released in response to pro-apoptotic stimuli. These diverse proteins include cytochrome c, AIF, Smac/Diablo, endonuclease G and Omi/HtrA2 (See e.g., Van Loo, et al. (2002) *Cell Death Differ*, 9, 1031-42). Each of these proteins has a distinct function but they are all pro-apoptotic and, invariably, their release from the mitochondria induces cell death. Omi/HtrA2, the most recent member of this group, was originally isolated and characterized as a new members of the stress-signaling pathway (Faccio, et al. (2000) *J. Biol. Chem.*, 275, 2581-8). Omi/HtrA2 has high sequence homology to bacterial HtrAs, proteins that act as chaperones at normal temperatures and as proteases at elevated temperatures to remove damaged or denatured proteins (Pallen, et al. (1997) *Mol. Microbiol.*, 26, 209-21).

Omi/HtrA2 is a human serine protease that has extensive homology to bacterial high temperature requirement A (HtrA) proteins (Faceio et al. (2000) *J Biol Chem.* 275, 2581-2588; and Gray et al. (2000) *Eur., J. Biochem.* 267, 5699-5710). Bacterial HtrAs have a dual function, acting as chaperones at normal temperatures and as proteases at elevated temperatures and removing damaged or denatured proteins, allowing the recovery and survival of bacteria following stress (Pallen et al. (1997) *Mol. Microbiol.* 26, 209-221; and Spiess et al. (1999) *Cell* 97, 339-347).

Mammalian Omi/HtrA is a ubiquitous protein, although tissue-specific alternatively spliced forms have been reported (Gray et al. (2000) *Eur., J. Biochem.* 267, 5699-5710; and Faccio et al. (2000) *Genomics* 68, 343-347). Recent studies described Omi as a mitochondrial protein that upon induction of apoptosis is released to the cytoplasm where it binds XLAP (X chromosome-linked inhibitor of apoptosis protein) resulting in caspase-9 activation (Suzuki et al. (2001) *Mol. Cell*. 8, 613-621; Hegde et al. (2002) *J. Biol. Chem.* 277, 432-438; Martins et al. (2002) *J Biol. Chem.* 277, 439-444; Verhagen et al. (2002) *J. Biol. Chem.* 277, 445-454; and van Loo et al. (2002) *Cell Death Differ*. 9, 20-26). In this regard, Omi resembles Smac/DIABLO, which also binds IAPs and as a result activates caspase-9 (Flu et al. (2000) *Cell* 102, 33-42; and Verhagen et al. (2000) *Cell* 102, 43-53).

Omi/HtrA2 protein is synthesized as a precursor that is processed in the mitochondria to produce the mature protein. This processing exposes an internal tetrapeptide motif, AVPS, at the amino terminus. A similar motif is found in all IAP-binding proteins, including the *Drosophila* Grim, Reaper, Hid, and Sickle (Chen et al. (1996) *Genes Dev.* 10, 1773-1782; Vucit et al. (1997) Proc. *Nail. Acad. Sci. US. A.* 94, 10183-10188; Vucic et al. (1998)*Mol. Cell. Biol.* 18, 3300-3309; and Srinivasula et al. (2002) Cur. *Biol.* 12, 125-130).

Omi/HtrA2 is present in the mitochondria and is released to the cytoplasm upon induction of apoptosis. In this capacity, Omi/HtrA2 is unique both in its structure as well as its function. In the cytoplasm, Omi/HtrA2 can induce apoptosis through a caspase-dependent as well as in a caspase-independent pathway.

Omi/HtrA2 belongs to a family of mammalian serine proteases; its proteolytic activity is necessary for auto-processing to expose the AVPS motif. Furthermore, Omi/HtrA2 can also induce apoptosis in a manner that does not depend on the AVPS motif but depends entirely on its ability to function as a protease (Suzuki, et al. (2001) *Mol. Cell.*, 8, 613-21; Hegde, et al. (2002) *J. Biol Chem*, 277, 432-8; Martins, et al. (2002) *J. Biol. Chem.*, 277, 439-44; and Verhagen, et al. (2002) *J. Biol. Chem.*, 277, 445-54). Thus suggests specific substrates for Omi/HtrA2 may exist and their cleavage (whether this leads to activation of a precursor or a destruction of a protein) may be a part of the apoptotic process. One other member of family of proteases is L56/HtrA1, is a serine protease that is overexpressed in osteoarthritic cartilage (Hu, et al. (1998) *J. Biol. Chem.*, 273, 34406-12) and is also repressed in fibroblasts following SV40 infection (Zumbrunn, et al. (1996) FEBS *Lett.*, 398, 187-92). The similarity between Omi/HtrA2 and other proteins is restricted to their carboxyl terminus which includes the proteolytic domain and PDZ motif while the amino termini of the two proteins are different (Faccio, et al. (2000) *J. Biol. Chem.*, 275, 2581-8). Unlike Omi/HtrA2, which remains intracellular, L56/HtrA 1 is secreted (Faccio, et al. (2000) supra; and Hu, et al. (1998) *J. Biol. Chem.*, 273, 34406-12).

When Omi/HtrA2 induces apoptosis in a caspase-independent pathway, it does so by relying entirely on its ability to function as a serine protease (Suzuki et al. (2001) *Mol. Cell*. 8, 613-621; Hegde et al. (2002) *J. Biol. Chem.* 277, 432-438; and Verhagen et al. (2002) *J. Biol. Chem.* 277, 445-454). Neither the mechanism nor the significance of this function of Omi/HtrA2 is clearly understood.

Figure 6:
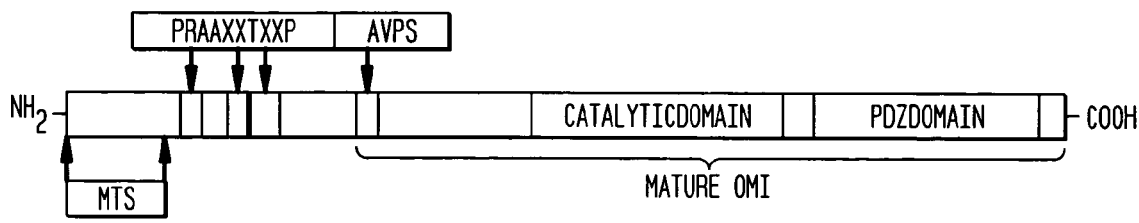
FIG. 6 is a schematic drawing showing the functional domains of Omi/HtrA2.

Structurally, Omi/HtrA2 is a 458 amino acid polypeptide that was originally isolated as an interactor of Mxi2 kinase (Faccio, et al. (2000) *J. Biol. Chem.*, 275, 2581-8). It was subsequently identified as an interactor of presenilin, a protein found mutated in some cases of Alzheimer's disease (Gray, et al. (2000) *Eur J Biochem*, 267, 5699-710). There are three distinct domains in the Omi/HtrA2 protein: a catalytic domain, a PDZ domain and an amino terminal domain (see FIG. 6). The amino-terminal domain carries a mitochondrial targeting sequence (MTS) and three copies of a motif PRAAXXTXX (SEQ ID No:1), where X is any amino acid. The function of this motif is not yet known. This amino terminal domain of Omi (aa 1-133) is cleaved through an intra-molecular reaction to create the mature Omi/HtrA2 protein. The mature Omi/HtrA2 has a new exposed amino terminal sequence (AVPS) that is similar to the sequence present in other known inhibitors of apoptosis (IAP)-binding proteins (See Table 1). This family of proteins includes the only other known IAP binding protein Smac/DIABLO (Du, et al. (2000) *Cell*, 102, 33-42; and Verhagen et al. *Cell*, 102, 43-53), as well as three *Drosophila* proteins Reaper (Vucic, et al. (1997) *Proc. Natl. Acad. Sci. USA*, 94, 10183-8; and Vucic, et al. (1997) *Mol Cell Biol*, 17, 667-76), Hid (Vucic, et al. (1998) *Mol Cell Biol*, 18, 3300-9) and Grim (Chen, et al. (1996) *Genes Dev*, 10, 1773-82). Besides the presence of the IAP-binding motif, no other similarity is found between these proteins.

TABLE 1

Comparison of known IAP-binding motifs found in two mammalian (Omi/HtrA2 and Smac/DIABLO) and three Drosophila proteins

| | |
|---|---|
| Omi/HtrA2 | AVPSPPPA |
| Smac/Diablo | AVPIAQKS |
| Reaper | AVAFYIPD |
| Hid | AVPFYLPE |
| Grim | AIAYFIPD |

Omi/HtrA2 mRNA is expressed ubiquitously, and the gene is localized on human chromosome 2p12. Omi/HtrA2 interacts with Mxi2, an alternatively spliced form of the p38 stress-activated kinase and, when made in a heterologous system, shows proteolytic activity against a non-specific substrate β-casein. The proteolytic activity of Omi/HtrA2 is markedly up-regulated in the mouse kidney following ischemia/reperfusion. (See Examples)

Figure 5:
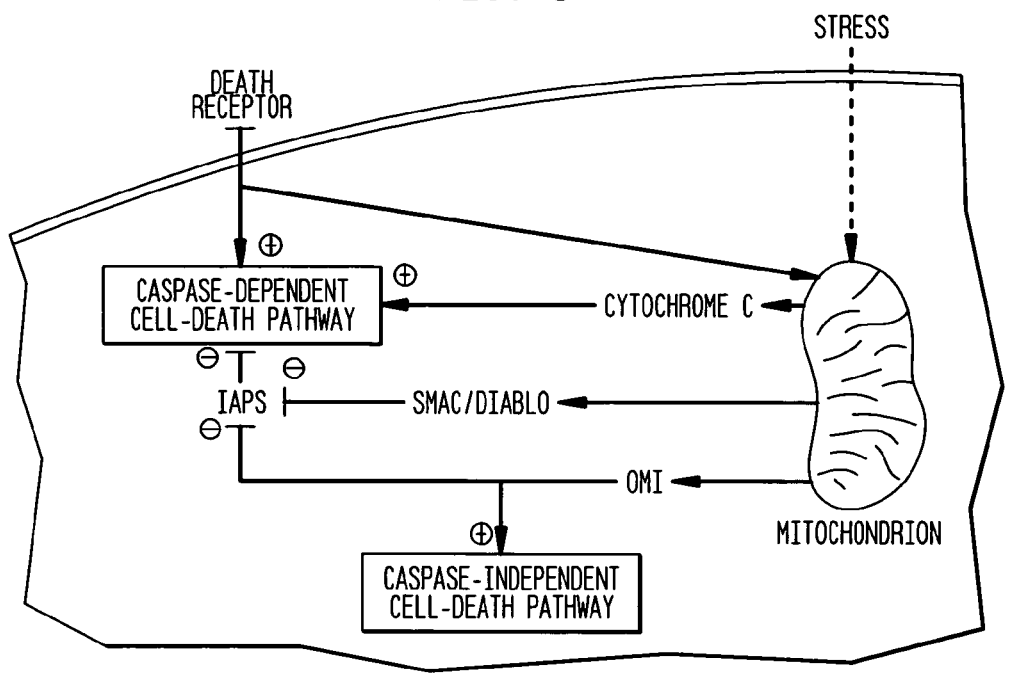
FIG. 5 is a schematic drawing showing caspase-dependent and caspase-independent pathways involving Omi/HtrA2.

Therefore, Omi/HtrA2 promotes cell death via two different pathways: one that relies on IAP binding and inhibition and involves caspase activation, and the second which depends on its proteolytic activity and is caspase-independent. (See FIG. 5)

Alternative forms of Omi/HtrA2 are also within the scope of the invention and include alternative splice forms and their encoded polypeptides. In one embodiment, the alternatively spliced form of Omi/HtrA2 is D-Omi that is expressed predominantly in the kidney (See Examples). To identify the origin of this alternatively spliced form, the genomic locus of Omi/HtrA2 was characterized and found to be present on the human chromosome 2p12. Omi gene consists of eight exons, two of them are absent in the kidney specific D-Omi. D-Omi is not able to bind to the Mxi2 protein due to its modified PDZ domain. Furthermore, D-Omi has no detectable proteolytic activity when tested against β-casein, a generic substrate.

D-Omi lacks the amino acid sequence encoded by two exons and is structurally quite distinct from Omi/HtrA2. It has a modified PDZ domain and shows no detectable proteolytic activity. The data shown in the Examples section suggest that D-Omi may have a unique function, different from Omi/HtrA2, in the tissues where it is expressed. D-Omi may also function in apoptosis and it may have role in modulating cellular events following tubular cell injury, such as renal tubule cell injury.

Variants of the Omi/HtrA2 nucleic acid molecules and the proteins they encode are also within the scope of the invention, these include natural variants (e.g., polymorphisms, splice variants or mutants) and those produced by genetic engineering (e.g., substitutions, deletions or addition of residues). Many methods for generating mutants have been developed (see generally, Ausubel et al., supra). Preferred methods include alanine scanning mutagenesis and PCR generation of mutants using an oligonucleotide containing the desired mutation to amplify mutant nucleic acid molecules. Variants generally have at least 70% or 75% nucleotide identity to the native sequence, preferably at least 80%-85%, and most preferably at least 90%, 92%, 93%, 94%, 95%, 96%, 97%, 98% or 99% nucleotide identity.

Further, a nucleotide variant will typically be sufficiently similar in sequence to hybridize to the reference sequence under moderate or stringent hybridization conditions. For nucleic acid molecules over about 500 bp, stringent conditions include a solution comprising about 1 M $Na^+$ at 25 to 30° C. below the Tm; e.g., 5×SSPE, 0.5% SDS, at 65 C.; see Ausubel et al., Current Protocols in Molecular Biology, Greene Publishing, 1995; Sambrook et al., Molecular Cloning: A Laboratory Manual, Cold Spring Harbor Press, 1989). Typically, homologous polynucleotide sequences can be confirmed by hybridization under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2.times.SSC, 0.1% SDS, 50° C. once, 30 minutes; then 2×SSC, room temperature twice, 10 minutes each, homologous sequences can be identified which contain at most about 25-30% basepair mismatches. More preferably, homologous nucleic acid strands contain 15-25% basepair mismatches, even more preferably 5-15% basepair mismatches.

The term "homology" or "identity" or "homologous" as used herein refers to the percentage of likeness between molecules. To determine the homology or percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identify" is equivalent to amino acid or nucleic acid "homology"). The percent identify between the two sequences is a function of the number of identical positions shared by the sequences, taking into account the number of gaps, and the length of each gap, which need to be introduced for optimal alignment of the two sequences.

The comparison of sequences and determination of percent identify between two sequences can be accomplished using a mathematical algorithm. For example, the percent identity between two amino acid sequences can be determined using the Needleman and Wunsch (1970) J Mol. Biol. (48):444-453) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, and 6. In another example, the percent identify between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In yet another example, the percent identify between two amino acid or nucleotide sequences is determined using the algorithm of E. Meyers and W. Miller (CABIOS, 4:11-17(1989)) which has been incorporated into the ALIGN program (version 2.0), using a PAM120 weight residue table, a gap length penalty of 12 and a gap penalty.

III. Omi/HtrA2 and Tubular Cell Death

In one aspect, the invention pertains to inhibiting tubular cell death by modifying apoptosis, preferably by modifying caspase-independent apoptosis. In a particularly preferred embodiment, the methods and compositions of the invention can be used for acute renal failure (ARF).

ARF is a serious medical problem that occurs in 5% of all hospitalized patients. The prognosis of ARF is poor, has remained unchanged over the past three decades, and carries a high mortality rate of about 50%. Although ARF is the result of many causes, the most common cause is injury to the renal tubular epithelial cells (RTEC).

The invention relates to the role of Omi/HtrA2 in the apoptotic cell death that occurs in RTEC, as well as the molecular events that follow its activation leading to apoptosis. By blocking the activity of Omi/HtrA2 using a specific inhibitor, a new approach to protect and maintain cell viability is available.

The cell death that follows renal injury is both apoptotic as well as necrotic (Lieberthal, et al. (1998) *Semin Nephrol*, 18, 505-18). The relative contribution of these two forms of cell death to tubular necrosis is not yet known. It depends both on the nature as well as severity of insult. Severe injury (e.g. ishcedmic injury) usually triggers necrosis whereas milder insults to the kidney cause apoptotic death of the RTEC. Necrosis is difficult to prevent but apoptosis can potentially be modulated to maintain cell viability. Therefore, identifying the different components of the apoptotic pathway, especially the ones that play a major role in kidney, provides new information on the apoptotic process. These new components can also provide specific and novel targets for intervention to help patients with acute renal failure.

Most of the previous studies on tubular apoptosis have focused on the role of caspases and their activation and have utilized caspase-specific inhibitors in an attempt to inhibit apoptosis and protect tubular cells from ischemic as well as toxic insults (See e.g., Ueda, et al. (2000) *Am J Med*, 108, 403-15; and Ueda, et al. (2000) *Nephrol Dial Transplant*, 15, 318-23). Omi/HtrA2 is a pro-apoptotic protease and is the only protein identified thus far that is able to cause apoptosis in a caspase-dependent as well as caspase-independent manner. The caspase-independent pathway is not yet clearly understood but relies on the ability of Omi/HtrA2 to function as a serine protease.

Table 2 lists known inducers of apoptosis of tubular cells in acute renal failure. Caspases have been shown to be activated both by ischemic as well as cytotoxic insults to cultured RTECs (Lau, et al. (1999) *Kidney Int*, 56, 1295-8; Hortelano, et al. (2000) *J Am Soc Nephrol*, 11, 2315-23; van de Water, et al. (2000) *J. Biol Chem*, 275, 25805-13. 2000; and Kaushal, et al. (2001) *Kidney Int*, 60, 1726-36) as well as kidney cells in vivo (Daemen; et al. (2001) *Transplantation*, 71, 778-84; Shi, et al. (2000) *Am J Physiol*, 279, F509-17; Sano, et al. (2000) *Kidney Int*, 57, 1560-70; and Bonventre, (1998) *Kidney & Blood Pressure Research*, 21, 226-9). Furthermore, inhibition of caspases ameliorates ischemia-reperfusion injury in the kidney (Daemen, et al. (1999) *J Clin Invest*, 104, 541-9).

TABLE 2

Potential causes of apoptosis of tubular cells in acute renal failure

| | |
|---|---|
| The default pathway of apoptosis | Grow factor deficiency: Rapamycin Loss of cell-matrix adhesion, Loss of cell-cell adhesion |
| Renal tubular cell injury | Ischemia/hypoxia: Oxidant stress Pharmacologic agents: Cisplatin, Aminoglycosides, Amphotericin B |
| Receptor-ligand interactions | Fas-FasL: TNF-α-TNF Receptor type 1, Angiotensin II-angiotensin II receptor type 2 (ATR2) |

Omi/HtrA2 plays a role in the apoptosis that occurs in RTECs following renal injury. The data in the Examples section shows that Omi/HtrA2 is predominantly expressed in the proximal tubular cells in both human and mouse kidneys. This area of the kidney is most susceptible to ischemic injury. The protein level of Omi/HtrA2 increased dramatically 24 hours after ischemia/reperfusion as well as in MPT cells treated with antimycin or cisplatin (inducers of apoptosis). The amount of Omi/HtrA2 protein increases dramatically after ischemic or chemical injury in the mouse kidneys or MPT cells. Furthermore, inhibiting the proteolytic activity of Omi/HtrA2 using the ucf-101 inhibitor protects MPT cells from cisplatin-induced apoptosis.

Though not bound by any theory, Omi/HtrA2 may exert its caspase-independent effect by proteolytic cleavage of potential substrates leading to the destruction and removal of the substrates as part of this process. Alternatively, Omi/HtrA2, through specific proteolytic cleavage, might activate precursor proteins that are part of the caspase-independent apoptotic process.

IV. Inhibitors

In one aspect, the invention pertains to using inhibitors of caspase-independent apoptosis. In order to investigate the caspase-independent mechanism of apoptosis initiated by Omi/HtrA2, specific inhibitors of its proteolytic activity were isolated. One such family of synthetic compounds was identified and described in the Examples section. In one embodiment, the apoptosis inhibiting compound include the class of heterocyclic compounds referred to as 1,3 diphenyl-5-(substituted)-2-thioxo-dihydropyrimidine-4,6-dione derivatives. In a preferred embodiment, the apoptosis inhibiting compound has the general structure shown in FIG. 1a, where $R_1$, depicts the various side chains which can include, but are not limited to a nitro group, a carboxy group, a hydroxide, an aliphatic group, an aromatic group, an acyl group, an alkoxy group, an alkylene group, an alkenylene group, an alkynylene group, a hydroxycarbonylalkyl group, an anhydride, an amide, an amine, and a heterocyclic aromatic group. In a preferred embodiment, the apoptosis inhibiting compound has the structure shown in FIG. 1b and is referred to as "ucf-101".

Figure 2A:
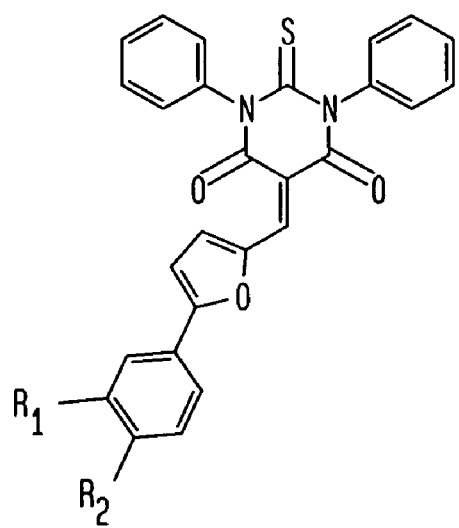
FIG. 2a is the general structure of an apoptosis inhibiting compound.
Figure 2B:
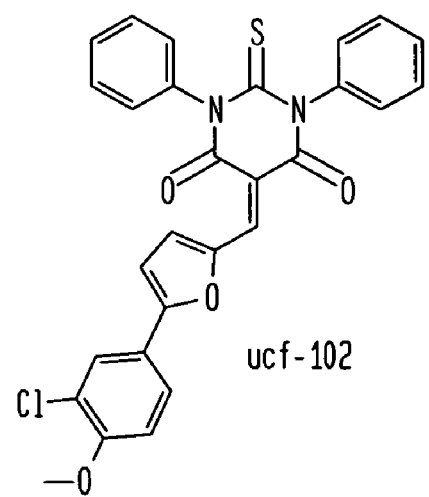
FIG. 2b is the specific structure of Ucf 102.

In another embodiment, the apoptosis inhibiting compound has a general structure shown in FIG. 2a, where $R_1$ is a nitro group, a carboxy group, a hydroxide, an aliphatic group, an aromatic group, an acyl group, an alkoxy group, an alkylene group, an alkenylene group, an alkynylene group, a hydroxycarbonylalkyl group, an anhydride, an amide, an amine, and a heterocyclic aromatic group. In a preferred embodiment the apoptosis inhibiting compound has the structure shown in FIG. 2b and is referred to as "ucf-102".

Figure 3A:
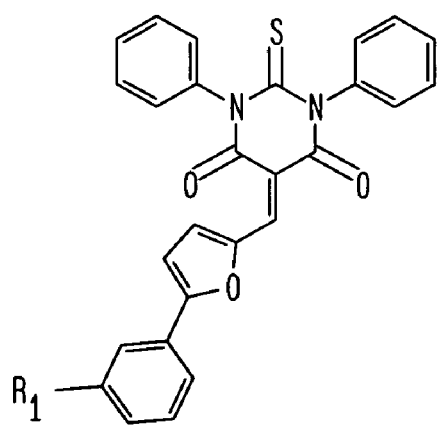
FIG. 3a is the general structure of an apoptosis inhibiting compound.
Figure 3B:
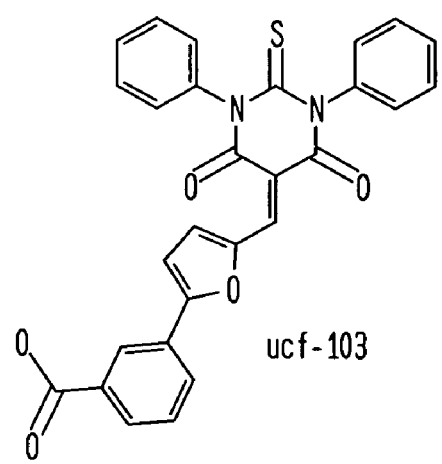
FIG. 3b is the specific structure of Ucf 103.

In another embodiment, the apoptosis inhibiting compound has the general structure shown in FIG. 3a, where $R_1$ is a nitro group, a carboxy group, a hydroxide, an aliphatic group, an aromatic group, an acyl group, an alkoxy group, an alkylene group, an alkenylene group, an alkynylene group, a hydroxycarbonylalkyl group, an anhydride, an amide, an amine, and a heterocyclic aromatic group. In preferred embodiment, the apoptosis inhibiting compound has the structure shown in FIG. 3b and is referred to as "ucf-103."

Figure 4A:
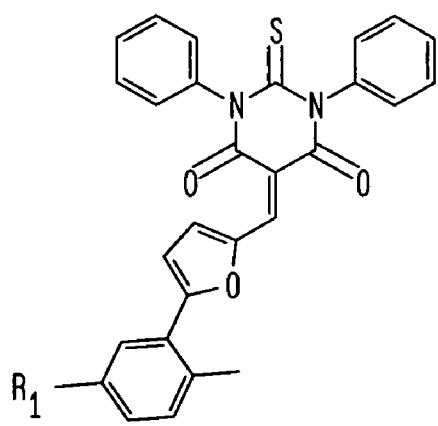
FIG. 4a is the general structure of an apoptosis inhibiting compound.
Figure 4B:
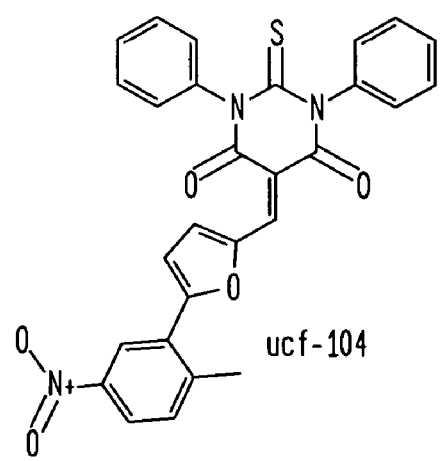
FIG. 4b is the specific structure of Ucf 104.

In another embodiment, the apoptosis inhibiting compound has the general structure shown in FIG. 4, where $R_1$ is a nitro group, a carboxy group, a hydroxide, an aliphatic group, an aromatic group, an acyl group, an alkoxy group, an alkylene group, an alkenylene group, an alkynylene group, a hydroxycarbonylalkyl group, an anhydride, an amide, an amine, and a heterocyclic aromatic group. In preferred embodiment, the apoptosis inhibiting compound has the structure shown in FIG. 4b and is referred to as "ucf-104".

These class of heterocyclic compounds showed significant and specific activity against the protease in an in vitro assay. The compound from this family, which exhibited the highest activity against Omi/HtrA2 is ucf-101. The results clearly showed ucf-101 had a profound effect on the activity of Omi/HtrA2 and could substantially inhibit its ability to induce caspase-independent apoptosis in caspase-9 (−/−) null fibroblasts. The results clearly showed ucf-101 had a profound effect on the activity of Omi/HtrA2 and could substantially inhibit its ability to induce caspase-independent apoptosis in caspase-9 (−/−) null fibroblasts.

Ucf-101 naturally fluoresces and easily enters mammalian cells, allowing its use in in vivo experiments. The ucf-101 inhibitor can therefore be used as a tool to dissect the two different activities (caspase-dependent versus caspase-independent) of Omi and their respective contribution to apoptosis in various biological settings. Furthermore, ucf-101, or a similar compound, may be useful as an anti-apoptotic drug that would specifically target caspase-independent cell death under clinical conditions.

V. Omi/HtrA2 Substrates

In one aspect, the invention pertains to identifying substrates involved in caspase-independent apoptosis. In particular, the identification of substrates of Omi/HtrA2. To identify Omi/HtrA2 substrates an assay for substrates can be performed. In general, assays are designed to evaluate apoptotic pathway activation (e.g., caspase protein processing, caspase enzymatic activity protease activity, cell viability, cell morphology changes, DNA laddering, and the like). In any of the assays, a statistically significant increase or decrease compared to a proper control is indicative of enhancement or inhibition. In a preferred embodiment, apoptosis is monitored by an electrophoresis method (e.g., 2D gel electrophoresis), where the presence, absence or disappearance if a protein is measured. In such an assay, cell extracts are incubated with recombinant Omi/HtrA2 (test sample) and without Omi/HtrA2 (control sample). After incubation, the cell extracts are examined by electrophoresis (e.g., 2D electrophoresis). Typically, the presence of a protein in the control sample, and its subsequent disappearance (or the degradation into smaller fragments) in the test sample, identifies the presence of a specific Omi/HtrA2 substrate in the cell extract. The disappearance of the protein band indicates that the protein is a specific substrate of Omi/HtrA2 which has been degraded by the protease activity of Omi/HtrA2.

Using this assay, the data shown in the Examples section identifies two substrates for Omi/HtrA2. In one embodiment, the Omi/HtrA2 substrate is the 14-3-3 protein. In another embodiment, the Omi/HtrA2 substrate is annexin V. The data shows that the two polypeptides were specifically cleaved by Omi/HtrA2 and their degradation was inhibited by the specific inhibitor ucf-101. Annexin V and 14-3-3 proteins were shown to be involved in both apoptosis and intracellular signaling.

VI. Screening for Inhibitor or Enhancers

In one aspect, the invention pertains to identifying inhibitors of apoptosis, particularly inhibitors of caspase-independent apoptosis. In particular, the identification of inhibitors of Omi/HtrA2. Candidate inhibitors may be isolated or procured from a variety of sources, such as bacteria, fungi, plants, parasites, libraries of chemicals, peptides or peptide derivatives, antibodies, and the like. Inhibitors may also be rationally designed, based on the protein structures determined from X-ray crystallography.

Without wishing to be bound to a particular theory or held to a particular mechanism, an inhibitor may act by preventing Omi/HtrA2 release from the mitochondria, interfering with Omi/HtrA2 binding to an IAP, inhibiting Omi/HtrA2 protease activity, or by other mechanisms. If the caspase dependent pathway is involved, the inhibitor may act to prevent caspase activity. Alternatively, if the capase-independent pathway is involved, the inhibitor may inhibit the proteolytic activity of Omi/HtrA2 when it acts as a serine protease Inhibitors may include small molecules (organic molecules), peptides, polypeptides, and antibodies, for example. In one embodiment, the inhibitors prevent apoptosis. Inhibitors should have a minimum of side effects and are preferably non-toxic.

Screening assays for inhibitors will vary according to the type of inhibitor and the nature of the activity that is being affected. Assays may be performed in vitro or in vivo. In general, assays are designed to evaluate apoptotic pathway activation (e.g., caspase protein processing, caspase enzymatic activity, serine protease activity cell viability, cell morphology changes, DNA laddering, and the like). In any of the assays, a statistically significant increase or decrease compared to a proper control is indicative of enhancement or inhibition. In a preferred embodiment, apoptosis is monitored by a fluorescent method. Typically, an increase in cell viability as compared to a control indicates the presence of an inhibitor, while a decrease in cell viability as compared to a control indicates the presence of an enhancer.

For a caspase-independent in vitro assay, a substrate of Omi/HtrA2 is fluorescently labeled with fluorescent marker (e.g. FITC), and fluorescently labeled substrate is incubated with recombinant Omi/HtrA2 (e.g., MPB-Omi$_{134-458}$). The fluorescent activity of substrate is measured using a fluorescent microscopy or a fluorescemeter. As the Omi/HtrA2 protease acts on the substrate, a change in the fluorescence can be measured. Using this fluorescent assay, inhibitor and enhancers of Omi/HtrA2 can be used and the change in fluorescence in the presence of an inhibitor or enhancer can be measured. To facilitate detection using the fluorescent method with a substrate labeled with a fluorescent marker (e.g., FITC, and the like) the substrate can be examined by fluorescence microscopy. Candidate compounds may be obtained from a variety of sources. For example, they may be produced recombinantly, purified from a natural source, or synthesized. Alternatively, candidate molecules may be identified by screening a library of compounds such as those available form Nanoysn. The preferred compound will be one that is able to inhibit apoptosis, preferably caspase-independent apoptosis. The candidate compounds can be at least partially purified, and most preferably, candidate compounds will be purified to near homogeneity. Appropriate controls depend upon the source of the candidate compound and might include, for example, extracts from cells transfected with control vector, or storage or reaction buffers.

For a caspase-dependent in vitro assay detecting inhibitors and enhancers of caspase-mediated apoptosis can be performed by examining the effect of a candidate compound on the activation of an initiator caspase (e.g., caspase 9) or an effector caspase (e.g., caspases 3-7). Briefly, procaspase 9, an IAP, cytochrome c, DATP, and an Omi peptide, polypeptide, functional variant, or functional equivalent are provided. The processing of caspase-9 into two subunits is assayed. Alternatively, caspase-9 enzymatic activity is monitored by adding procaspase-3, procaspase-7, or other effector caspases to the reaction mix and monitoring the activation of these caspases, for example, either via subunit formation or via cleavage of a substrate (e.g., acetyl DEVD-aminomethyl coumarin (amc), lamin, PRPP, PARP, and the like). Typically, an increase in processing to subunits indicates the presence of an enhancer, while a decrease in processing to subunits indicates the presence of an inhibitor.

Also, for caspase-dependent apoptosis a candidate compound may be used for binding assays. A candidate compound may be added to a binding reaction with an Omi binding molecule and recombinant Omi/HtrA2 peptide or polypeptide, and its ability to inhibit Omi/HtrA2 binding to an Omi-binding molecule can be determined by comparing binding in the presence or absence of a candidate compound. In certain circumstances, such assays will detect displacement or inhibition of binding of an Omi-binding molecule from an Omi peptide or polypeptide.

In vivo assays are typically performed in cells transfected either transiently or stably with an expression vector containing an Omi/HtrA2 nucleic acid molecule such as those described herein. These cells may be used to measure caspase processing, caspase substrate turnover, enzymatic activity of effector caspases, or apoptosis in the presence or absence of a candidate compound. When assaying apoptosis, a variety of methods of cell analyses may be used, including, for example, fluorescent spectroscopy and electro-proteins dye staining and microscopy to examine cell viability, nucleic acid fragmentation, porosity of the cells, and membrane blebbing.

A variety of methodologies exist that can be used to investigate the effect of a candidate compound. Such methodologies are those commonly used to analyze enzymatic reactions and include, for example, SDS-PAGE, 2D-gel electrophoresis, fluorescent spectroscopy, fluorescent microscopy, HPLC analysis, autoradiography, chemiluminescence, chromogenic reactions, and immunochemistry (e.g., blotting, precipitating, etc.).

VII Pharmaceutical Compositions

The apoptosis inhibiting compound can be incorporated into pharmaceutical compositions suitable for administration to a subject, e.g., a human. Such compositions typically comprise the apoptosis inhibiting compound and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a receptor protein or anti-receptor antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

VIII Uses

In one aspect, the invention can be used to prevent, reduce, or ameliorate disorders associated with apoptosis. Examples of disorders associated with apoptosis include, but are not limited to, ischemia-reperfusion injury (e.g., stroke, myocardial infarction), heart failure—(e.g., loss of myocardiocytes); neurodegeneration disorders—(e.g., Alzheimer's disease, Parkinson's disease, Huntington's disease and amytrophic lateral sclerosis); inflammation; osteoarthritis; human immunodeficiency virus—(loss of *T lymphocytes*); bacterial infection—(apoptosis-inducing virulence proteins are secreted into the cytosol of host cell. e.g., *Shigella* species, *Salmonella* species, *Yersinia* species and *Chlamydia* species); allograft rejection and graft versus host disease; type 1 diabetes; and, trauma (spinal-cord injury, brain injury).

Other embodiments and used of the invention will be apparent to those skilled in the art from consideration of the specification and practice of the invention disclosed herein. All U.S. Patents and other references noted herein for whatever reason are specifically incorporated by reference.

EXAMPLES

Example 1

Methods and Materials (i) Preparation of FITC-labeled, Dephosphorylated casein

Casein-Dephosphorylated-casein (Sigma, 3 ml of 2 mg/ml stock solution) was used in a dialysis cassette (Pierce) placed in labeling buffer (0.03 mg/ml FITC, 50 mM sodium borate, pH 9.3, 40 mM NaCl) and kept for 48 h at 4° C. in the dark with constant stirring. After labeling, the FITC-dephosphorylated casein (Dcasein-FITC) was further dialyzed against 50 mM Tris-HCl, pH 7.5, and 50 mM NaCl to remove any residual unlabeled FITC. The Dcasein-FITC conjugate was recovered from the dialysis cassette and stored at 4° C. in the dark.

(ii) Expression and Purification of MBP-Omi and MBP-L56

Proteases-PCR was used to amplify DNA sequences corresponding to Omi/HtrA2 (amino acids 134-458) and L56/HtrA1 (amino acids 140-480). The PCR products were digested with MfeI and XbaI and cloned in the corresponding EcoRI and XbaI restriction sites of pMAL-p2X vector (New England Biolabs). MBP-Omi-(134-458) and MBP-L56-(140-480) proteases were expressed in TB1 *Escherichia coli* (New England Biolabs) and purified on an amylose binding affinity column as described by the manufacturer (New England Biolabs). The concentration of purified proteases was determined using the Bradford assay.

(iii) Expression and Purification of His-tagged Omi-(134-458)

PCR was used to amplify the DNA sequence corresponding to Omi/HtrA2 (Omi-(134-458)). The PCR product was cloned in-frame in the bacterial expression vector pET-28 (Novagen). For bacterial expression, BL21 (DE3) (Novagen) bacteria were transformed with pET-Omi-(134-458). Single colonies were grown overnight in LB medium containing kanamycin. The overnight culture (1 ml) was used to inoculate 1 liter of LB medium, and growth was continued at 37° C. until the $A_{600}$ was ~0.8. At this time, 1 mM mist isopropyl-1-thio-β-D-galactopyranoside was added, and the culture was placed in a shaking incubator overnight at 20° C. Bacteria were harvested by centrifugation and lysed in a buffer containing 20 mM Tris-HCl, pH 7.5, 500 mM NaCl, 100 μg/ml lysozyme, and a protease inhibitor mixture (Sigma). The bacterial suspension was then sonicated, and the soluble fraction was purified using nickel-nitrilotriacetic acid His-Bind resin (Novagen). The purity of the HisOmi-(134-458) protein was monitored by SDS-PAGE and Coomassie Blue staining of the resulting gel.

(iv) Proteolytic Activity of Omi Using Dcasein-FITC as Substrate

Opaque microtiter plates (coming Glass) were used in order to minimize background absorbance. A typical assay included 10 μg of Dcasein-FITC substrate, 2 μg of MBP-Omi-(134-458) in assay buffer (20 mM $Na_2HPO_4/NaH_2PO_4$, pH 7.4, 200 mM NaCl, 5% glycerol) in a final volume of 100 μl. Dcasein-FITC conjugate solution (50 μl of a 0.2 μg/μl stock solution) was added in each well using a Multidrop 384 multiple dispenser (Labsystems) and incubated in the Wallac 1420 Victor$^2$ Multilabel counter at 37° C. for 15 min. After this time, 50 μl of MBP-Omi-(134-458) protease (40 ng/μl) was added to each well. The fluorescence (535 nm) of the reactions was recorded every 5 min for a 30-min period.

(v) Combinatorial Library Screening

A Pharma Library Collection from Nanoscale Cominatorial Synthesis Inc., 625 Clyde Ave, Mountain View, Calif. 94943-2213 was screened for compounds, which may inhibit the proteolytic activity of MBP-Omi-(134-458) in an in vitro assay. Each compound, (from a total of 528 compounds) 10 µM final concentration, was preincubated with 50 µl of MBP-Omi-(134-458) (2 µg) for 15 min at 37° C. After this time, Dcasein-FITC solution (10 µg) was added, and the change in fluorescence was read every 5 min during a 30-min period using a 535-nm bandpass filter. The proteolytic activity of MBP-Omi-(134-458) was expressed as the percentage inhibition, where 100% refers to the activity in the absence of inhibitor (Me$_2$SO replaced the inhibitor in the assay).

(vi) Activity of Several ucf Analog Compounds against MBP-Omi-(134-458)

The assay was performed as described above using Dcasein-FITC as substrate. 2 µg of MBP-Omi-(134-458) was incubated with various concentrations of ucf-101, ucf-102, ucf-103, or ucf-104 for 15 min. After this time 10 µg of Dcasein-FITC substrate was added, and the reaction proceeded for an additional 30 min. The activity of MBP-Omi-(134-458) was monitored at 535 nm.

(vii) Determination of IC$_{50}$ for ucf-101 and ucf-102.

The IC$_{50}$ value for each of the two selected inhibitors was obtained using His-Omi-(134-458) and the EnzCheck assay kit (Molecular Probes) that contains BODIPY FL-casein as a generic substrate. Briefly, 35 µl of His-Omi (134-458) (500 nM) diluted in 20 mat Na$_2$HPO$_4$/NaH$_2$PO$_4$, pH 7.4, 200 mM NaCI, 5% glycerol was incubated with 5 µl of various concentrations of the inhibitors (0.1-1000 µM) in 100% Me$_2$S0 (final concentration of Me$_2$SO was 10%); 10 µl of BODIPY-FL casein (2.5 µM final concentration) diluted in buffer was added. The assay was carried out using 384-well microtiter plates. Fluorescence was monitored continuously for 10 min at 37° C. on a Tecan SpectraFluorPlus microtiter plate reader (Tecan, Crailsheim, Germany) at an excitation wavelength 485 nm/emission wavelength 530 nm. IC$_{50}$ values were calculated using the GraFit 4 program (Erithacus Software, Middlesex, UK).

(viii) Activity of ucf-101 Against Various Serine Proteases

The amount of the inhibitor giving a 50% (IC$_{50}$) decrease of the enzyme activity compared with the control reaction was estimated for various serine pro-teases. Briefly, 35 µl of the indicated enzyme diluted in the corresponding buffer was incubated for 10 min with 5 µl of various concentrations of inhibitor (0.1-1000 µM) in 50% Me$_2$50, 50% buffer. After this time, 10 µl of the corresponding peptidic colorimetric or fluorogenic substrate diluted in buffer was added. In the case of the FVIIa/TF assay, a preincubation of both proteins for 10 min at room temperature was performed prior to addition of the inhibitor to allow complex formation. For this experiment the following materials were used: canine FXa, rat FXa, and rabbit FXa (Enzyme Research Laboratories); trypsin from bovine pancreas and human thrombin (Sigma); human plasmin, human t-PA, human t-PA, and human kallikrein (Calbiochem-Novabiochem); human APC and recombinant human factor VIIa (American Diagnostica); and recombinant tissue factor (Dade Behring). The substrates used are as follows: spectrozyme FXa fluorogenic (American Diagnostica); kallilkrein fluorogenic substrate; protein C-activated substrate (Calbiochem); Chromozym X, Chromozym P1, and Chromozym t-PA (Roche Diagnostics); I-1045, I-1140, and I-1140 (Bachem).

The amount of each enzyme and its corresponding substrate used in the assay was canine FXa (2 nM), spectrozyme fXa fluorogenic (20 µM), rat FXa (5 nM), spectrozyme fXa fluorogenic (25 µM), rabbit FXa (5 nM), spectrozyme FXa fluorogenic (15 µMr), kallilkrein (5 nM), kallikrein fluorogenic substrate (50 µM), trypsin (2.5 nM), Chromozym X (150 µM), plasmin (5 nM), I-1045 (100 µM) thrombin (4 nM), Chromozym PL (150 µM), FVIIa/tissue factor (15 nM/3 nM), Chromozym t-PA (500 µM), t-PA (100 nM), I-1140 (200 µM), u-PA (3 nM), I-1140 (150 µM), activated protein C (5 nM), and protein C-activated substrate (100 µM) in a final concentration of 5% Me$_2$SO. All enzymatic assays were carried out at room temperature in 384-well microtiter plates (Nunc). Color development due to the release of p-nitroanilide from the chromogenic substrates was monitored continuously for 20 min at 405 nm on a Tecan SpectraFluorPlus microtiter plate reader (Tecan). fluorescence from the release of the coumarin derivative, aminomethylcoumarin, was measured at excitation 360 nm/emission 465 nm on the same reader. The IC$_{50}$ values were calculated using the GraFit 4 program (Erithacus Software).

(ix) Subcellular Localization of ucf-101

HeLa cells were grown on coverslips using F-12 (Ham's) nutrient mixture (Invitrogen) supplemented with 10% fetal calf serum (Sigma), 2 mM L-glutamine, 100 units/ml penicillin, and 100 µg/ml streptomycin (Invitrogen). Different concentrations of ucf-101 were added to the cell media, and after 2 h cells were washed three times with phosphate-buffered saline and fixed with 4% paraformaldehyde. The coverslips were then placed on glass slides using Fluoromount-G solution (Southern Biochemical Association). The subcellular localization of ucf-101 was monitored using a LSM510 confocal laser-scanning microscope (Zeiss).

(x) ucf-101 Inhibits Omi-induced Caspase-independent Apoptosis in Caspase-9–/–) Null Fibroblasts-Caspase-9(–/–) cells were transfected with either pEGFP-N1 vector (Clontech) or M-Omi-GFP that encodes a cytoplasmic form of Omi/HtrA2 (Hegde et al (2002) J. Biol. Chem. 277, 432-438). Transfected cells were kept in medium containing different concentrations of ucf-101. This medium, including the inhibitor, was replaced every 12 h. After 36 h, cells were stained with propidium iodide and 4',6-diamidino-2-phenylindole as described (Hegde et al (2002) J. Biol. Chem. 277, 432-438). Normal and apoptotic GFP-expressing cells were counted using fluorescence microscopy.

HeLa cells were transfected with mature Omi (aa134-458), Omi-A VPS-GFP and mature Omi where the first Alanine (A) was mutated to a Glycine. Omi-GVPS-GFP transfected cells were treated with increasing concentration of ucf-101. Overexpression of mature Omi-GVPS-GFP can induce apoptosis only through its ability to function as an active protease (caspase-independent pathway). ucf-101 inhibited the protease activity and apoptosis.

(xi) Kidney Ischemia/Reperfusion

Kidney ischemia/reperfusion experiments were performed using Balb/c male mice, 20-25 grams, which were anesthetized with sodium pentobarbital (65 mg/kg) i.p. and undergo uninephrectomy of the left kidney followed 24 h later by ischemia of the right kidney. This is done by placement of a microaneurysm clamp on the renal artery and vein for 30 min followed by reperfusion (104). Kidneys were harvested 1, 24, and 48 h after reperfusion.

In bilateral ischemia experiments, ischemia were performed for 30 min followed by reperfusion (Kelly, et al. (1996) J Clin Invest, 97, 1056-63). Kidneys will be harvested at the same time points as with nephrectomy/unilateral ischemia. Equal amounts of protein extracts from control and post-ischemic kidneys will be resolved and analyzed by SDS-PAGE. The level of Omi/HtrA2 protein will be determined by Western blot analysis using a specific antibody (Hegde, et al. (2002) *J. Biol Chem*, 277, 432-8; and Faccio, et al. (2000) *J. Biol. Chem.*, 275, 2581-8).

(xii) Immunohistochemistry

Kidneys from control or post-ischemic mice were briefly perfused in situ via the heart with PBS (0.9% NaCl in 10 mM sodium phosphate buffer, pH 7.4), followed by 2% paraformaldehyde, 70 mM lysine, and 10 mM sodium periodate (PLP) and fixed as (Breton, et al. (1998) *J Am Soc Nephrol*, 9, 155-66). Kidney slices were immersed in 30% sucrose then frozen in liquid nitrogen Semithin (1 mm). Sections were cut from tissue embedded in LX-112 and treated for 2 minutes with a mixture of 2 g KOH, 5 ml propylene oxide, and 10 ml methanol to remove the resin. Alternatively, 1 and 5 mm cryostat sections were used. Sections will be incubated for 10 min in PBS containing 1% BSA to reduce non-specific background staining, followed by a 2-hour incubation at room temperature with a 20-1 drop of specific antibody. After 3×5-min rinses in PBS, sections were incubated for 1 h with goat anti-rabbit IgG coupled to fluorescein isothiocyanate (Calbiochem-Behring Corp., San Diego, Calif.), and diluted 1:30 for detection of antigenic sites by immunofluorescence microscopy. Sections were then rinsed 3×5 min in PBS and mounted in Gelvatol containing 4% n-propyl gallate (Sigma Chemical Co., St. Louis, Mo.) to retard quenching of the fluorescence. Photographs of sections were taken on Kodak TMAX film using a Nikon FXA photomicroscope with epifluorescence. Some sections were also analyzed using the ABC-peroxidase procedure. After incubation with the primary IgG, a biotinylated goat anti-rabbit IgG (Vector Laboratories, Burlinghame, Calif.) were applied to sections for 1 hour, followed by the ABC reagent (also from Vector Laboratories) for a further 1 hour. Peroxidase was revealed with diaminobenzidine and $H_2O_2$, and the sections dehydrated in ethanol and mounted in Permount (Fisher Scientific Co.).

(xiii) Cell Culture

HK-2 cells were grown in DMEM/HamF12 media supplemented with 10% FCS, hydrocortisone (0.4 µg/ml), insulin, transferring and sodium selenite (all used at a final conc. 5 µg/ml). LLC-PK1 cells were grown in DMEM plus 10% FCS and MDCK in MEM plus 10% FCS.

(xiv) Isolation of Mouse Primary Kidney Proximal Tubular (MPT) Cells

MPT cells were isolated from collagenase-digested fragments derived from the cortices of kidneys of C57BL6 mice as described (Sheridan, et al. (1993) *Am J Physiol*, 265, F342-50; and Kroshian, et al. (1994) *Am J Physiol*, 266, F21-30). MPT cells were grown in serum-free medium (1:1 mixture of Dulbecco's modified Eagle's medium (DMEM) and Ham's F-12) containing 15 mM Hepes, 5 µg/ml insulin, 50 nM hydrocortisone, 5 µg/ml apotransferrin, 50 µg/ml penicillin, and 50 µg/ml streptomycin. The cells were used between the 5th and 10th day after culture.

(xv) Confocal Microscopy

Mouse proximal tubular cells were grown for 6 days on microscope cover slides. Adherent cells were washed in PBS, fixed in 4% paraformaldehyde and made permeable using ice-cold acetone. Non-specific binding was blocked with 2% BSA in PBS and, subsequently, cells were stained using a rabbit anti-Omi and a mouse anti-gp330 antibodies at room temperature for 2 hours. After three washes with PBS, secondary antibodies cy3 conjugated anti-rabbit and Oregongreen conjugated anti-mouse was added for one hour. Finally, the cover slips were washed and placed on microscope slides using Fluoromount-G as the mounting solution. Slides were observed using a LSM510 confocal laser scanning microscope (Zeiss).

(xvi) ATP Depletion of MPT Cells Using Chemical Anoxia

MPT cells were incubated in dextrose-free DMEM at 37° C. in a humidified atmosphere containing 5% $CO_2$-95% air. For control monolayers, not subject to ATP depletion, dextrose (10 mM) will be added to the DMEM medium. ATP depletion of varying severity was induced using 2 mM antimycin (Sigma) or 5 mM 2-deoxyglucose (DOG) (Sigma) with and without varying concentrations of dextrose. Antimycin alone causes the most severe ATP depletion and induces cell death by necrosis. DOG alone causes intermediate ATP depletion and induces apoptotic cell death (95). Six different metabolic conditions were used: 1) antimycin alone, 2) antimycin+0.25 mM dextrose, 3) antimycin+1 mM dextrose, 4) DOG alone, 5) DOG+4 mM dextrose, and 6) DOG+10 mM dextrose.

(xvii) Cisplatin-Induced Apoptosis

MPT cells was plated in serum-free medium [1:1 mixture of DMEM and Ham's F-12] (GIBCO) containing 2 µM glutamine, 50 U/ml penicillin, 50 mg/ml streptomicyn (GIBCO), 15 mM HEPES, 5 mg/ml transferring, 5 mg/ml insulin and 50 nM hydrocortisone (Sigma). Medium was replaced every 2 days and the cells were used 6 to 8 days later. The MPT cells were incubated with various concentrations (10, 20, 50, and 100 mM) of cisplatin or vehicle (methylformamide) for 48 hours and analyzed by Flow Cytometry, or extracts were prepared for Western blot analysis.

(xviii) Induction of Apoptosis on HK-2 Cell Line Using $H_2O_2$

HK-2 cells were cultured in DMEM medium containing 2 mM glutamine, 50 U/ml penicillin, 50 µg/ml streptomycin (GIBCO), 15 mM HEPES, 5 mg/ml apotransferrin, 5 mg/ml insulin and 50 nM hydrocortisone. Approximately 90% confluent cells were treated with various concentrations of $H_2O_2$ (10, 20, 50, 100 µM) for 18 hours. Whole cell extracts were prepared and analyzed by Western blot analysis using Omi/HtrA2 antibodies.

(xix) Use of siRNAs to Suppress Omi/HtrA2 Expression in Proximal Tubular Cells

The pSuppressor2 vector available from Imgenex (San Diego, Calif., Paul, et al. (2002) *Nat Biotechnol*, 20, 505-8) was used to stably express the small interfering RNA (siRNA) that is homologous to Omi/HtrA2 mRNA sequence.

A double stranded (ds) oligo with the following sequence was used:

```
5'-TCGAATTCGCTGGGGGAGGAGACagtactGTCTCCTCCCCCAGCGAATTTTT-3' (SEQ ID NO: 2)

3'-TAAGCGACCCCCTCCTCTGtcatgaCAGAGGAGGGGGTCGCTTAAAAATCTAG-5' (SEQ ID NO: 3)
```

This double stranded oligo encodes 19 base pairs representing sequence 51-70 nucleotides downstream of the initiation of translation of Omi/HtrA2. The sense and antisense sequence is separated by a stem loop of 6 nucleotides that encodes the Sca I restriction site used for easy identification of the insert. The double stranded oligo was cloned into the corresponding sites of the pSupressor2 vector and bacterial clones was screened by isolating plasmid DNA followed by restriction digest with Sca I restriction enzyme. Positive clones will have their plasmid DNA sequenced as described by Faccio, et al. ((2000) *J. Biol. Chem.*, 275, 2581-8). The pSuppresor/Omi clone was used to transfect HK-2 cells. The vector has the NeoR gene and permanent cell lines can be made using G418 (Invitrogen) in the culture medium. The effectiveness of this siRNA to suppress expression of the Omi/HtrA2 will be monitored by Western blot analysis using total cell extracts and anti-Omi antibodies. As a control, cell lines were made using the pSuppressor2 vector alone.

(xx) Cell Viability Assay

The viability of cells was monitored using the MTT assay (Buttke, et al. (1993) *J Immunol Methods*, 157, 233-40; and Mossman, (1983) *Environ Health Perspect*, 53, 155-61). The assay is based on the ability of the mitochondria of viable cells to cleave the tetrazolium rings of the pale yellow MTT dye to form dark blue formazan crystals. The amount of formazan product produced is directly proportional to the number of viable cells present in the culture well. After removal of the medium, MTT (1 µg/ml) is added to each well and incubated at 37° C. for 4 hours. The formazan crystals formed by viable cells are then dissolved by adding 10% SDS/0.01N HCl to each well and incubating overnight. The absorbance of aliquots from each well will be read by 1420 Multilabel counter Victor$_2$ (Wallac) plate reader with a test wavelength of 570 nm and a reference wavelength of 650 nm. Percent viability will be expressed as the absorbance of ATP-depleted cells with the ucf-101 inhibitor/absorbance of ATP-depleted cells without the inhibitor, where DMSO is added instead.

(xxi) Transfection of Mammalian Cells

60% confluent cells were transfected using the Lipofectamine Plus Reagent according to the instructions provided by the manufacturer (Life Technologies).

(xxi) Quantitative Real-Time PCR Analysis of Omi/HtrA2 mRNA.

Total RNA was isolated from MPT cells using the QIAgen RNeasy kit following manufacturer's instructions. 2 µg of total RNA was transcribed into cDNA using the Omniscript reverse transcriptase (QIAgen). Real-Time PCR was performed with AmpliTaq Gold polymerase in a iCycler real-time PCR thermocycler (BioRad) and the SyBr Green detection protocol as per the manufacturer's instructions. Briefly, 12 ng of total cDNA, 50 nM of each primer and 1×SyBr Green mix was used in a total volume of 25 µl. The primer sequences for murine Omi/HtrA2 are: Sense 5'-GCGGGGCGGGGTG-CAAAC-3' (SEQ ID NO: 4) and antisense 5'-GACAGC-CAGCACCGTGG-3' (SEQ ID NO: 5). Murine b-actin primers: sense 5'-TTCGTTGCCGGTCCACA-3' (SEQ ID NO: 6) and antisense 5'-ACCAGCGCAGCGATATCG-3' (SEQ ID NO: 7). Samples were read in triplicate and normalized for expression of β-actin RNA.

(xxii) Western Blot Analysis

For Western blot analysis, cells were harvested 24 hours after transfection, washed and lysed using a Triton X-100 based buffer (1% Triton X-100, 10% Glycerol, 150 mM NaCl, 20 mM Tris-HCl pH 7.5, 2 mM EDTA) containing a protease inhibitors cocktail (Roche). Approximately 30 µg of the whole cell extracts were re-suspended in SDS-sample buffer and boiled for 3 minutes. The samples were resolved by SDS-PAGE and electro-transferred onto PVDF membranes (Pall Corporation) using a Semi-Dry Transfer Blot (Bio-Rad). Non-specific binding was blocked using 2% nonfat dry milk in TBST to saturate the membrane. The blot was then incubated with an anti-GFP monoclonal antibody (Santa Cruz Biotechnology), 1:700 dilution followed by a secondary horseradish peroxidase-conjugated goat anti-mouse antibody (Jackson ImmunoResearch), 1:15000 dilution, and visualized by chemiluminescence (ECL) using a SuperSignal West Pico substrate (Pierce).

(xxiii) Flow Cytometry

Cells were grown on 6 well plates using appropriate media. 60% confluent cells were transfected with various constructs using Lipofectamine Plus Reagent according to the instructions provided by the manufacturer (Life Technologies). The transfected cells were detached 48 hours later, washed twice with ice-cold PBS, resuspended in 1× binding buffer (BD Bioscience) and stained with PE-conjugated annexin V according to BD Bioscience protocol. Analysis of GFP and annexin V positive cells will be performed on a FACS Vantage Flow Cytometer (Becton Dickinson).

Example 2

Activity of Omi Protease Against Dcasein-FITC

This example demonstrates the activity of Omi protease against Dcasein-FITC. As no physiological substrates for Omi protease are known, β-casein was used as a generic substrate in in vitro assays to monitor the protease activity of Omi. For high throughput screening, a new assay was developed that uses a mixture of α-casein, β-casein, and dephosphorylated casein (Dcasein) coupled to FITC, as a substrate, The use of Dcasein-FITC increases the fluorescence during the reaction with less fluctuation and lower background (data not shown). A typical assay uses 10 µg of Dcasein-FITC and 2 µg MBP-Omi-(134-458) in 100 µl of reaction buffer (20 mM sodium phosphate buffer, pH 7.5, 200 mM NaCl, and 5% glycerol) at 37° C. for 30 min.

The results show that there was a rapid increase in fluorescence for the first 20 min followed by a slower increase for the remaining 10 min of the assay. Various concentrations of substrate, Dcasein-FITC, as well as MBP-Omi-(134-458) were used for kinetic studies.

Example 3

Combinatorial Library Screening

By using an in vitro high throughput assay system, a combinatorial library of synthetic compounds (Nanosyn) was screened. This collection represented compounds that had commonly accepted pharmaceutical hit structures with possible pharmacological properties. The assay was performed in multiple 96-well plates. The inhibition activity of each compound was expressed as the percentage of relative fluorescence change (decrease) compared with the control (no compound). The final concentration of each compound tested was 10 µM. Fifty two compounds showed more than a 20% inhibition of MBP-Omi-(134-458) activity in the initial screening, but only one compound (ucf-101) showed greater than a 50% inhibition at the concentration tested after two rounds of screening and selection (Table III).

TABLE III

Screening for inhibitors of the proteolytic activity of Omi
A combinatorial library of 528 selected compounds was used in a high
throughout screening for potential inhibitors of the proteolytic activity of
Omi. Several compounds had weak activity against Omi, but after two
rounds of selection only one chemical showed substantial and
reproducible inhibition against Omi in the assay used.

| % inhibition | 1st screening | 2 screening |
|---|---|---|
| 0 | 6 | 26 |
| 1-19 | 468 | 47 |
| 20-39 | 52 | 1 |
| 40-59 | 2 | 1 |
| Total | 528 | 75 |

Example 4

Figure 7:
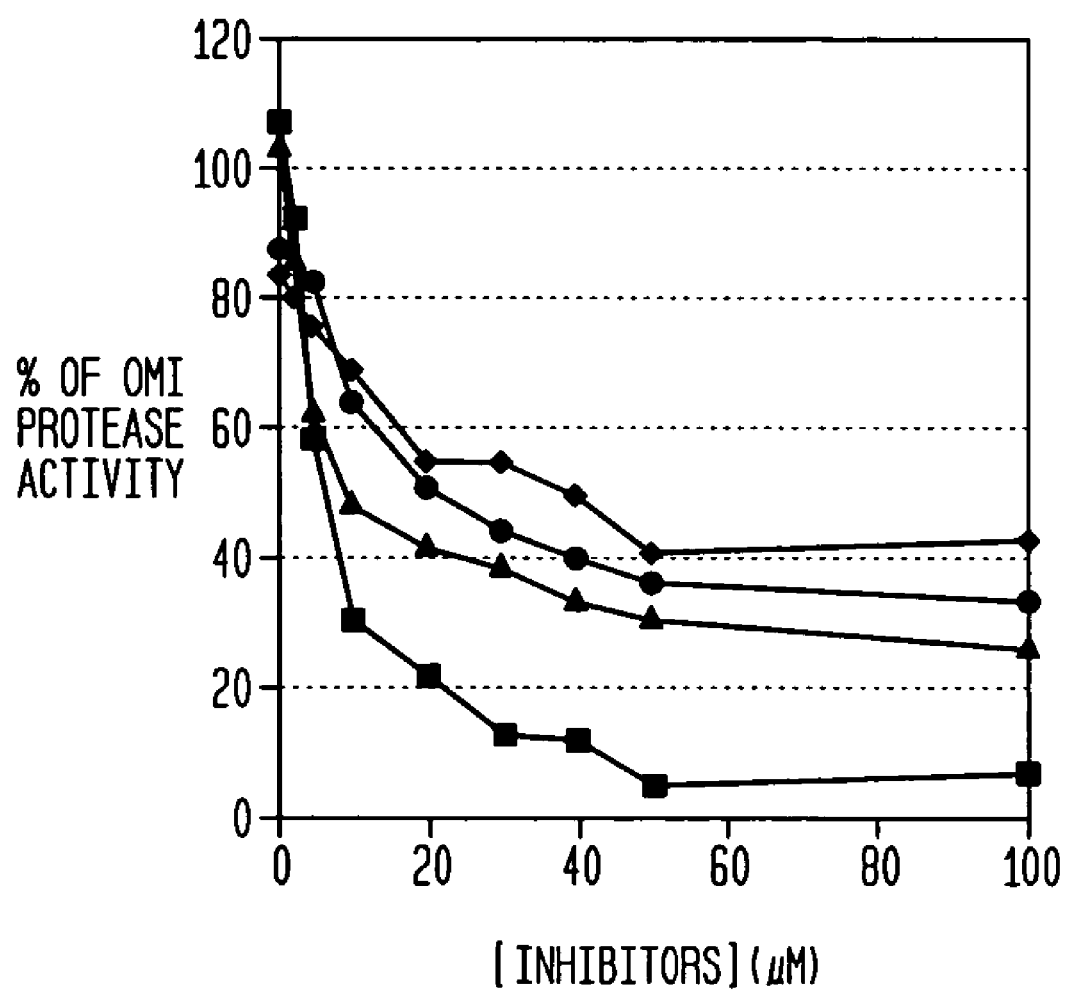
FIG. 7 is a graph showing the inhibition of MBP-Omi (134-458) in the presence of ucf-101 and several other ucf analogs.

Inhibition of the Proteolytic Activity of MBP-Omi-(134-458) Using ucf-101 and Various Analogs Several analogs of ucf-101 were obtained, and the chemical structures are shown in FIGS. 1-4. The activity of these ucf analogs was tested using MBP-Omi-(134-458) in the same in vitro assay system. FIG. 7 shows the inhibition of MBP-Omi-(134-458) by ucf-101 and several other ucf analogs. The assay was performed with 10 μg of Dcasein-FITC incubated with 2 μg of MBP-Omi-(134-458) in the presence of various concentrations of ucf-101 and three analogs, ucf-102, ucf-103, and ucf-104. ■, ucf-101; ▲, ucf-104; ●, ucf-103; ♦, ucf-102. All three analogs inhibited the proteolytic activity of MBP-Omi-(134-458) but to a lesser extent than ucf-101. ucf-104 (20 μM) inhibited 58% MBP-Omi-(134-458) activity, whereas the same concentration of ucf-101 inhibited more than 78% MBP-Omi-(134-458) activity. When MBP-Omi-(134-458) was preincubated with various concentrations of ucf-101, -102, -103, and -104 at 37 C. for longer periods (40 mill or 1 h) inhibition was reduced, indicating the inhibitors did not irreversibly bind the enzyme (results not shown). MBP-Omi-(134-458) was also incubated with various amounts of Dcasein-FITC in the presence of 10 μM ucf-101. The rate of the reaction decreased by 50% when the concentration of the substrate was doubled and even reached the rate of the control reaction at higher concentrations of Dcasein-FITC (results not shown). These results suggest ucf-101 is a competitive inhibitor of Omi protease.

Example 5

Assay of His-Omi-(134-458) Activity Using Unlabeled β-Casein and SDS-PAGE Analysis The inhibitory effect of ucf-101 on the activity of His-Omi-(134-458) was monitored by incubating inhibitor and enzyme together for 10 min at room temperature prior to the addition of β-casein as a generic substrate. An in vitro assay of the proteolytic activity of His-Omi-(134-458) in the presence of different concentrations of ucf-101 was performed, and the results shown in FIG. 8. The assay was performed at 37° C., and after the indicated time points the reactions were resolved on SDS-PAGE and the gel stained with Coomassie Blue. Omi (200 ng) was incubated with 5 μg of β-casein substrate in a 20 μl reaction volume for 30 min at 37° C. The ucf-101 compound was preincubated with His-Omi-(134-458) (His-Omi) protease for 10 min at room temperature prior to the addition of β-casein substrate. (Lane 1, β-casein control; lane 2, His-Omi+β-casein, digested for 15 min; lane 3, His-Omi+β-casein, digested for 30 min; lane 4, His-Omi+100 μM ucf-101+/β-casein; lane 5, His-Omi+80 M ucf-101+β-casein; lane 6, His-Omi+50 μM ucf-101+β-casein; lane 7, His-Omi+30 μM ucf-101+β-casein; lane 8, His-Omi+20 μM ucf-101+β-casein; lane 9, His-Omi+10 pM ucf-101+β-casein; and lane 10, prestained molecular weight marker.)

Figure 8:
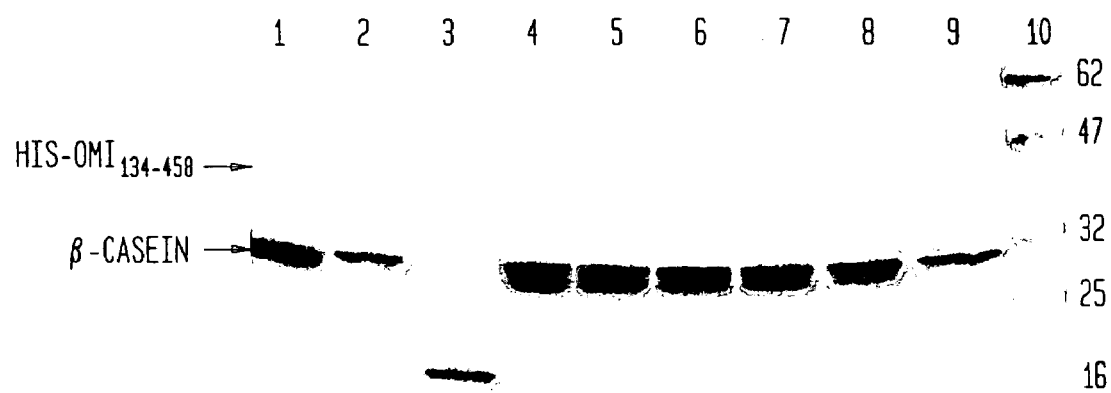
FIG. 8 is a photograph of an SDS-PAGE gel showing the in vitro proteolytic activity of MBP-Omi (134-458) in the presence of different concentrations of ucf 101.

FIG. 8 shows that bacterially made His-Omi-(134-458) had substantial activity against β-casein, and after 30 min total degradation of the substrate occurred. ucf-101 inhibited His-Omi-(134-458) activity in a concentration-dependent manner (lanes 4-9) when assayed for 30 min with 200 ng of His-Omi-(134-458) and 5 μg of β-casein. ucf-101 (80 μM) was able to inhibit completely the activity of 200 ng of His-Omi-(134-458) (lane 5).

Example 6

Comparison of the Proteolytic Activities of His-Omi (134-458) and His-L56-(156-480)

Figure 9:
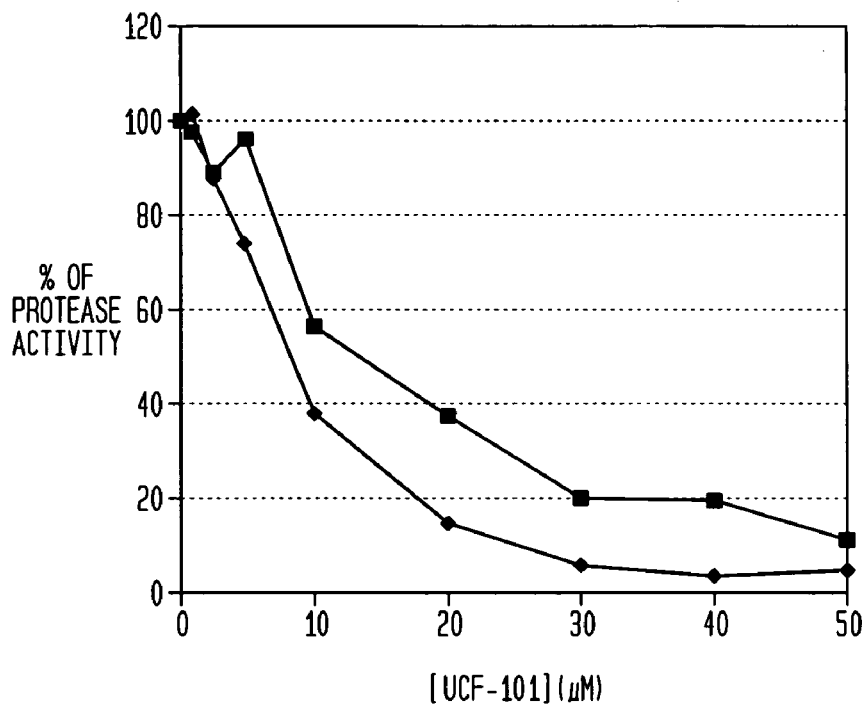
FIG. 9 is a graph showing the inhibition of proteolytic activity of MBP-Omi (134-458) and MBP-L56 (14-480)

Proteins-OmiHtrA2 and L56/HtrA1 are members of the same family of mammalian serine proteases with extensive homology in their catalytic domains (Faceio et al. (2000) *J. Biol. Chem.* 275, 2581-2588). Bacterially made His-Omi-(134-458) and His-L56-(140-480) was used to investigate whether ucf-101 was able to inhibit the activity of His-L56-140-480) in a similar manner. FIG. 9 shows the inhibition of the proteolytic activity of MBP-Omi-(134-458) and MBP-L56-(140-480) by ucf-101. The assay was performed with 10 jig of FITC-Dcasein and 2 μg of MBP-Omi-(134-458) (MBP-Omi) or MBP-L56-(140-480) (MBP-L56) in the presence of various concentrations of ucf-101. The increase in fluorescence for the initial 20 min was used for comparing the activities of MBP-Omi-(134-458) or MBP-L56-(140-480). ♦, MBP-Omi; ■MBP-L56.

FIG. 9 shows ucf-101 is an effective inhibitor of the activity of His-L56-(140-480) but to a lesser extent than His-Omi-(134-458).

Example 7

$IC_{50}$ of ucf-101 Against Various Serine Proteases

The enzymatic activity of His-Omi and the determination of the $IC_{50}$ for ucf-101 and ucf-102 were performed as described in Example 1 (vii). These values are shown in Table IV. ucf-101 had an $IC_{50}$ of 9.5 μM, and ucf-102 had an $IC_{50}$ of 45.9 μM.

TABLE IV $IC_{50}$ of ucf-101 and ucf-102 inhibitors on His-Omi
The value is the average from three independent experiments.

| Inhibitors | $IC_{50}$ in μM |
|---|---|
| ucf-101 | 9.5 |
| ucf-102 | 45.9 |

The specificity of ucf-101 was determined using several unrelated serine proteases. Their susceptibility to inhibition by ucf-101 was tested. The $IC_{50}$ values for ucf-101 inhibitor from these experiments are shown in Table IV. These results suggest ucf-101 has very high specificity for the Omi protease.

TABLE IV

IC$_{50}$ values of ucf-101 on various protease
The two IC$_{50}$ values are derived from two independent experiments.
The two IC$_{50}$ values are derived from two independent experiments.

| Protease | IC$_{50}$ in μM |
| --- | --- |
| Canine-Fxa | 430 |
|  | 360 |
| Rat-Fxa | 410 |
|  | >500 |
| Rabbit-Fxa | 260 |
|  | 300 |
| Hu-kallikrein | 200 |
|  | 250 |
| Bovine-trypsin | >500 |
|  | >500 |
| Hu-plasmin | >500 |
|  | 400 |
| Hu-thrombin | >500 |
|  | >500 |
| Hu-rec.-FVIIa | >500 |
|  | >500 |
| Hu-t-PA | 390 |
|  | 390 |
| Hu-u-PA | 500 |
|  | 500 |
| Hu-APC | 500 |
|  | 500 |

Example 8

Intracellular Localization of ucf-101

To investigate the potential use of ucf-101 inhibitor in in vivo experiments, the ability of the inhibitor to enter mammalian cells was tested. ucf-101 has natural fluorescence at 543 nm that was used to detect the presence of the compound. HeLa cells were treated with different concentrations of ucf-101 and observed by confocal microscopy. Intense red fluorescence, due to the presence of ucf-101, was observed in the cytoplasm of the treated cells.

The cytoplasmic localization of ucf-101 was examined when subconfluent HeLa cells were treated with 50 (A), 40 (B), and 20 μM (C) ucf-101 and were observed using a confocal microscope. A-C show cytoplasmic red staining due to the presence of ucf-101, indicating cells are permeable to this chemical. No staining was seen when Me$_2$SO alone was used. D (results not shown)

Example 9 ucf-101 Can Inhibit Omi-Induced Caspase-Independent Apoptosis

The inhibition of Omi-induced caspase independent cell death by ucf-101 was examined. Mouse embryo caspase-9 (−/−/−) null fibroblasts (Hakem et al. (1998) Cell 94; 339-352) were transiently transfected with pEGFP-N1 (control) or Omi-GFP (Hegde et al, Supra). The transfected cells were kept in medium containing different concentrations of ucf-101. The percentage of apoptotic cells in the transfected population was determined after 36 h as described by Hakem et al. (1998), Supra.

Figure 10:
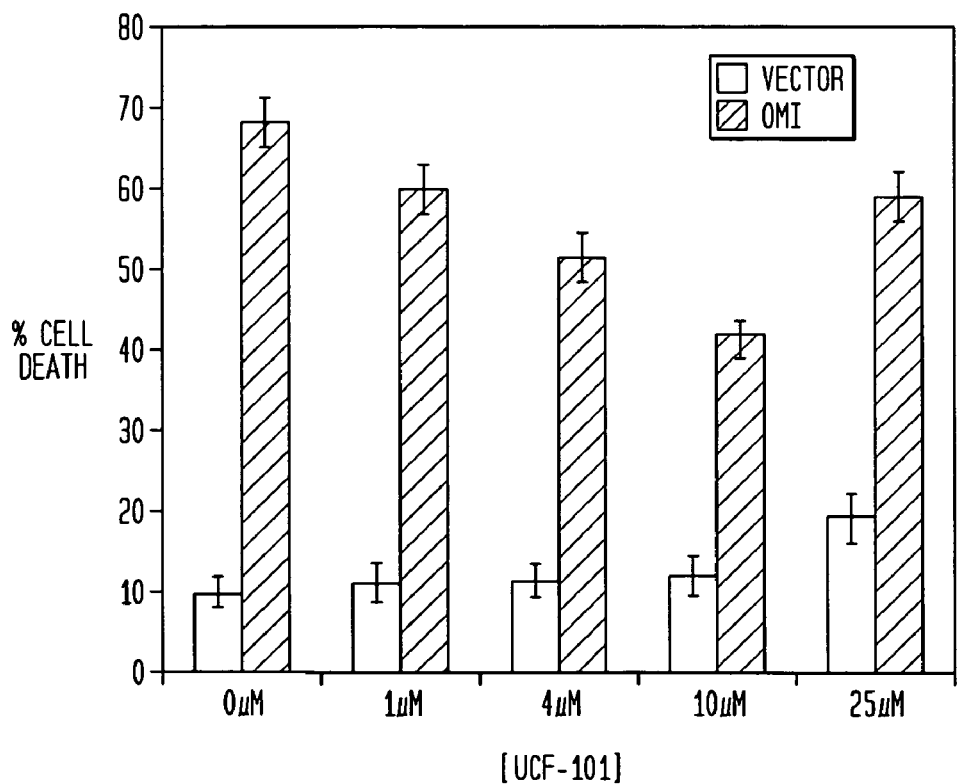
FIG. 10 is a bar graph showing the inhibition of Omi-induced caspase independent cell death by ucf-101.

Cytoplasmic expression of M-Omi-GFP induced apoptosis in ~70% of the transfected cells. When cells were treated with increasing concentrations of ucf-101, it was found that increasing the concentration of inhibitor up to 10 μM gradually reduced Omi-induced apoptosis up to 40%. ucf-101 had no effect on the control (vector alone) transfected cells. When the concentration of the ucf-101 increased to 25 μM, the anti-apoptotic activity of the inhibitor was compromised due to a cytotoxic side effect that caused apoptosis both in the M-Omi-GFP, as well as control transfected cells (FIG. 10).

Collectively, these results demonstrate that Omi/HtrA2 is a mitochondrial serine protease that is released to the cytoplasm upon induction of apoptosis. In the cytoplasm, Omi binds to XIAP and relieves its inhibition of caspase-9 (Suzuki et al. (2001) *Mol. Cell.* 8, 613-621; Hegde et al. (2002) *J. Biol. Chem.* 277, 432-438; and Verhagen et al., (2002) *J. Biol. Chem.* 277, 445-454). In this respect, Omi acts in a manner similar to Smac/DIABLO, another mitochondrial protein that also binds to XIAP (Du et al. (2000) *Cell* 102, 33-42; and Verhagen et al., (2000) *Cell* 102, 43-53). This interaction with XIAP is mediated via an AVPS motif that is exposed at the amino terminus of mature Omi protein after processing (Suzuki et al. Supra, Hegde et al. Supra).

Omi/HtrA2 is also able to induce apoptosis in a caspase-independent manner that exclusively relies on its ability to function as a protease (Suzuki et al. (2001) *Mol. Cell.* 8, 613-621; Hegde et al. Supra; Martins et al. (2002) *J. Biol. Chem.* 277, 439-444; Verhagen et al. Supra; and van Loo et al. (2002) *Cell Death Differ.* 9, 20-26). This caspase-independent pathway is not well understood; its contribution to overall cell death is not known, and the role of Omi as a protease in this pathway is not clear. Because the caspase-independent pathway relies on the ability of Omi/HtrA2 to function as a protease, it suggests that proteolytic cleavage of specific proteins is involved. This cleavage might inactivate and remove apoptotic inhibitors, or it may activate precursor proteins whose function might be necessary for caspase-independent cell death.

In order to investigate the contribution of the proteolytic activity of Omi to its overall pro-apoptotic function, specific inhibitor(s) of its activity were screened. One such specific inhibitor was identified and called ucf-101. This heterocyclic compound was able to inhibit the proteolytic activity of Omi in vitro in a very specific and reversible manner. The specificity of ucf-101 was tested against a panel of several unrelated serine proteases, and no significant activity was detected. When L56/HtrA1 was used in the same assay, ucf-101 showed specific inhibition against this protease. L56/HtrA1 belongs to the same family of proteases as Omi, and they both share extensive homology throughout their respective catalytic domains (Faceio et al. (2000) *J. Biol. Chem.* 275, 2581-2588). The normal function of L56/HtrA2 is not known, and unlike Omi that localizes to mitochondria, L56 is secreted (Ru et al. (1998) *J. Biol. Chem.* 273, 34406-34412). The natural fluorescence of ucf-101 was used to monitor its ability to enter mammalian cells. This property is necessary for ucf-101 to be useful for in vivo experiments designed to test inhibition of Omi that is intracellular.

To test the ability of ucf-101 to inhibit the proteolytic activity of Omi in vivo, an assay was used where transient overexpression of a cytoplasmic form of Omi induces caspase-independent cell death (Hedge et al, supra). The cells used in this assay were caspase-9 (−/−) null mouse embryonic fibroblasts (Hakem et al. supra)) in which over-expression of a cytoplasmic form of Omi can induce the caspase-independent pathway of apoptosis. This form of cell death caused by Omi relies entirely on its ability to function as a protease. Therefore, if ucf-101 blocks the activity of Omi, it will interfere with apoptosis of the caspase-9 (−/−) mouse embryonic fibroblasts. When these fibroblasts were transfected with the vector encoding the cytoplasmic Omi and treated with ucf-101, apoptosis was dramatically reduced.

Example 10

Omi/HtrA2 is Predominantly Expressed in the Proximal Kidney Tubules

To determine the expression profile of Omi/HtrA2 in kidney cells, immunocytochemical staining for Omi/HtrA2 was performed as described (Faccio et al. (2000). *J. Biol. Chem.*, 275, 2581-8 and Park, et al (2002) *J. Biol Chem*, 277, 2040-9)). Human kidney sections were obtained from Biochain Institute Inc. (Hayward, Calif.) and mouse sections were prepared as previously described (Faccio et al (2000 Supra). Omi/HtrA2 antiserum was raised against bacterially made His-tagged Omi/HtrA2 protein (residues 134-458) and affinity purified (Hegde, et al (2002) Supra). Proximal tubules were identified by apical staining with anti-gp-330 (also known as megalin) (green) (Kerjaschki, et al (1982) PNAS, 79, 5557-81). Omi/HtrA2 protein expression was indicated by red staining; when both images are merged there was extensive co-localization of gp330 and Omi/HtrA2. Both human and mouse kidney sections showed the same expression profile.

Example 11

Expression of Omi/HtrA2 is Upregulated After Ischemia/Reperfusion

To show that Omi/Htra2 was upregulated after ischemia/reperfusion, Balb/c male mice underwent uninephrectomy of the left kidney and, 24 hours later, ischemia was induced on the right kidney for 30 min followed by reperfusion (Park, et al. (2002) *J. Biol Chem.*, 277, 2040-9). Kidneys were harvested 90 min and 24 hours after reperfusion and processed as described in Example 1 (xi). Sections of mouse kidneys showed a substantial increase in the intensity of Omi/HtrA2 staining 90 min and 24 hours after ischemia/reperfusion as compared with sham perated kidneys with Anti-Omi having a red fluorescence and anti-gp330 having a green fluorescence (data not shown).

Example 12

Expression of Omi/HtrA2 Protein in Proximal Tubule (MPT) Cells

To investigate the expression of Omi/HtrA2 protein in proximal tubule (MPT) cells, MPT cells were isolated from the kidneys of 4-5 week old mice as described in the Example 1. Confocal microscope images of two representative populations of MPT cells were stained with anti-Omi (red) and anti-gp330 (green). Mouse proximal tubular cells were grown for 6 days on microscope cover glass. Adherent cells were stained using a rabbit anti-Omi and a mouse anti-gp330 at room temperature for 2 hours. Secondary antibodies used were: cy3 conjugated anti-rabbit and Oregon-green conjugated anti-mouse. Images were obtained using a LSM510 confocal laser scanning microscope (Zeiss). MPT cells were stained with anti-Omi/HtrA2 (A1 and B1). The same MPT cells were stained with anti-gp330 antibodies (green) (A2 and B2). Merged images of 1 and 2 (A3 and B3). Nomarsky images (A4 and B4). The results show that all MPT cells identified by staining with anti-gp330 also stained positive with anti-Omi/HtrA2 (data not shown).

Example 13

Subcellular Localization of Omi/HtrA2 in Normal and Apoptotic MPT Cells

The subcellular localization of Omi/HtrA2 in normal and apoptotic MPT cells was investigated by as described in Example 1. Confocal microscope images of normal or apoptotic MPT cells stained with anti-Omi (red) and MitoTracker (green) (data not shown). Apoptosis was induced using 2 μM Antimycin for 1 hour. Omi antibody staining was done as described in Example 1. 50 nM of MitoTracker dye was added for 20 minutes. MPT cells stained with anti-Omi/HtrA2 (red) (1). The same MPT cells stained with anti-gp330 antibodies (green) (2) and Nomarsky images of the MPT cells were also produced. The results show that Omi/HtrA2 protein and distinct punctate perinuclear staining in normal MPT cells and co-localizes with mitochondrial staining. After induction of apoptosis MPT cells show more intense Omi/HtrA2 staining that is more diffuse and extends throughout the cell.

Example 14

The Protein Level of Omi/HtrA2 Increases in MPT Cells Induced with Various Apoptotic Stimuli To investigate the protein level of Omi/HtrA2, MPT cells were isolated and exposed to different concentrations of cisplatin for 48 hours, or they were treated with 2 μM antimycin for different time periods. Approximately 5 μg protein of total cell extract was resolved by SDS-PAGE, PAGE, transferred to a PVDF membrane and probed using the anti-Omi antibodies as described in Example 1.

Figure 11A:
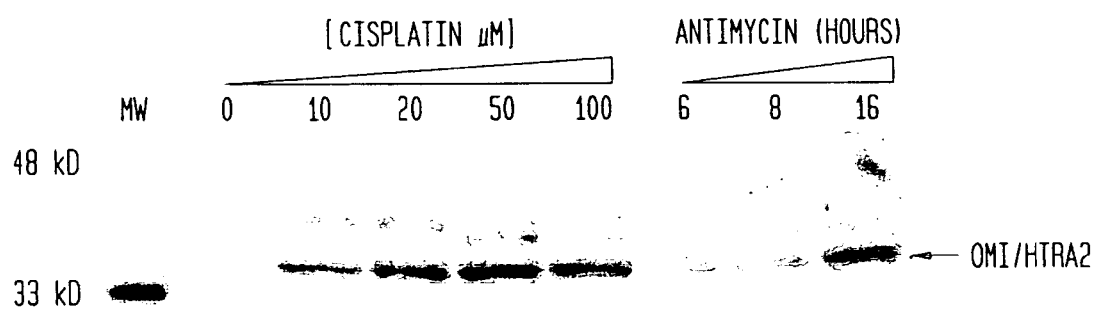

Western blot analysis showed up-regulation of Omi/HtrA2 protein following induction of apoptosis (See FIG. 11*a*). Both cisplatin and antimycin treatment induced expression of Omi/HtrA2 protein in MPT cells.

Figure 11B:
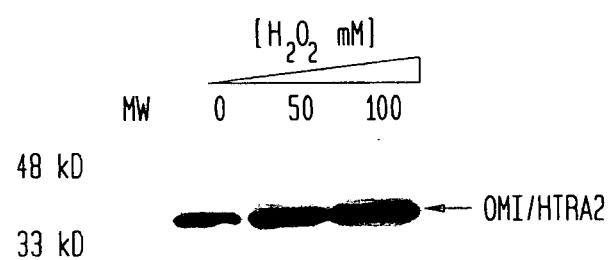
FIG. 11b shows the increase in the presence of hydrogen peroxide.

A Western blot analysis of Omi/HtrA2 protein in HK-2 (human proximal tubular epithelial cell line) cells after induction of apoptosis using the indicated concentrations of $H_2O_2$ for 18 hours is shown in FIG. 11*b*. The results show that the basal protein level of Omi/HtrA2 is higher in HK-2 cells than in primary MPT cells. In the HK-2 cell line, there is also substantial increase in the level of the Omi/HtrA2 protein after induction of apoptosis with $H_2O_2$.

Example 15

Ucf-101 Protects MPT Cells from Cisplatin-Induced Apoptosis

This example describes the protective effects of an inhibitor of apoptosis, Ucf-101 on cisplatin-induced apoptosis. Cisplatin used at low doses can also induce apoptosis in RTECs whereas high doses induce necrosis (Lieberthal, et al. (1996) *Am J Physiol*, 270, F700-8; and Lau, et al. (1999) *Kidney Int*, 56, 1295-8). Early animal studies have shown apoptosis to occur in rat kidney cortexes 12 hours after ischemia/reperfusion (Schumer, et al (1992) *Am J Pathol*, 140, 831-8). More studies have described apoptosis to occur in ischemia/reperfusion injury to the kidney (Nakajima, et al. (1996) *Am J Physiol*, 271, F846-53; Yin, et al. (1997) *J. Biol Chem*, 272, 19943-50; Nogae, et al. (1998) *J Am Soc Nephrol*, 9, 620-31; and Raafat, et al. (1997) *Shock*, 8, 186-92). Ucf-101 was isolated for its ability to inhibit the proteolytic activity of Omi/HtrA2 in vitro (Cilenti, et al. (2003) *J. Biol Chem*, 278, 11489-94).

The ability of ucf-101 to passively enter mammalian cells makes it possible to be used for in vivo studies. It was hypothesized that if Omi/HtrA2 through its proteolytic activity plays a role in tubular cell death following renal injury, ucf-101 inhibitor will have a protective anti-apoptotic function in the same system. Previous studies have shown that treatment of MPT cells with cisplatin caused increased expression of p53, and this induction of p53 was necessary and essential for cisplatin-induced apoptosis (Cummings, et al. (2002) *J Pharmacol Exp Ther*, 302, 8-17; and Xiao, et al. (2003) *J Toxicol Environ Health A*, 66, 469-79). Furthermore, a recent report showed that Omi/HtrA2 expression is directly regulated by p53 at least in HeLa cells (Jin, et al. (2003) *Genes Dev*, 17, 359-67). It was therefore hypothesized that Omi/HtrA2 was involved in the cisplatin-induced apoptosis as a downstream effector of p53 and ucf-101 was tested as an inhibitor of in cisplatin-induced apoptosis.

Figure 12:
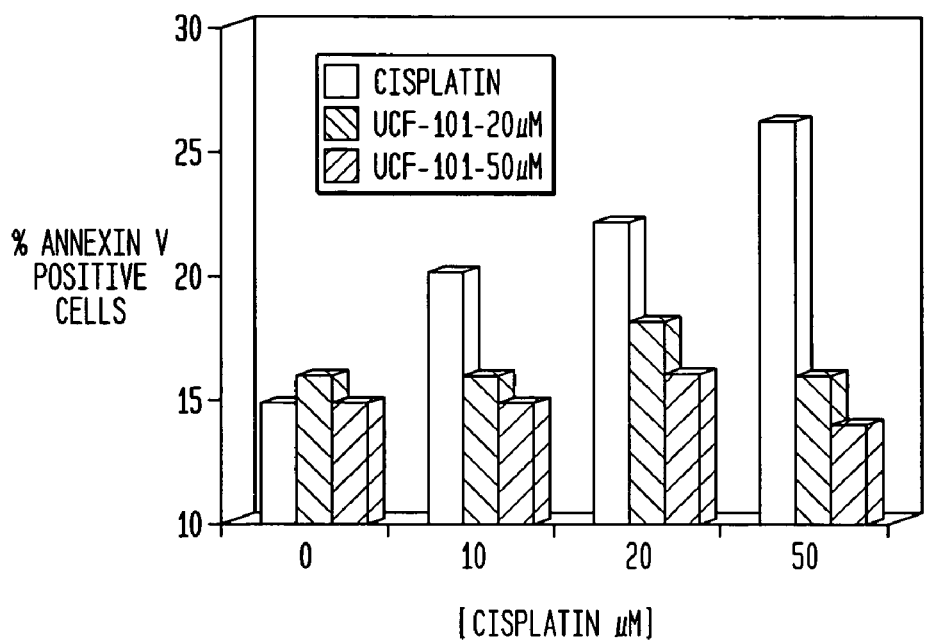
FIG. 12 is a bar graph showing that ucf-101 blocks cisplatin-induced apoptosis in MPT cells.

FIG. 12 shows that ucf-101 blocks cisplatin-induced apoptosis in MPT cells. MPT cells were treated with either 20 μM or 50 μM ucf-101 for 20 minutes. After this time, apoptosis was induced with different concentrations of cisplatin for 6 hours. Cells were detached, washed with PBS and stained with annexin V according to BD Biosciences protocol. Analysis of annexin V positive cells was performed on a FACS Vantage Flow Cytometer (Becton Dickinson). Results shown are the average values from three independent experiments. The data shows that ucf 101 reduces apoptosis in a dose-dependent manner in cisplatin induced apoptotic cells.

Collectively, the data shows that Omi/HtrA2 is expressed in the kidney proximal tubules, an area highly susceptible to injury and cell death. Furthermore, the protein level of Omi/HtrA2 dramatically increased after kidney ischemia/reperfusion in MPT cells treated with antimycin or cisplatin as well as in HK-2 cells treated with $H_2O_2$. Finally, ucf-101, a specific inhibitor of the proteolytic activity of Omi/HtrA2, protects MPT cells from cisplatin-induced apoptosis. These results suggest that Omi/HtrA2 plays an important role in injury/apoptosis that occurs in proximal tubule cells following ischemic or chemical insult.

Example 16

The Function of D-Omi

This example investigates the roles of D-Omi, a kidney-specific, alternatively spliced form of Omi/HtrA2. Omi/HtrA2 is expressed ubiquitously but recently an alternatively spliced form (D-Omi) has been isolated by this group, and is found predominantly in the kidney and to a lesser extent in the colon and thyroid (Faccio, et al. (2000) *Genomics*, 68, 343-7). D-Omi lacks the amino acid sequence encoded by exons 3 and 7 that affects both its catalytic domain as well as the PDZ domain. The function of D-Omi is not known. Its restricted tissue-specific expression might suggest a specific role in the organs where it is found.

Figure 13:
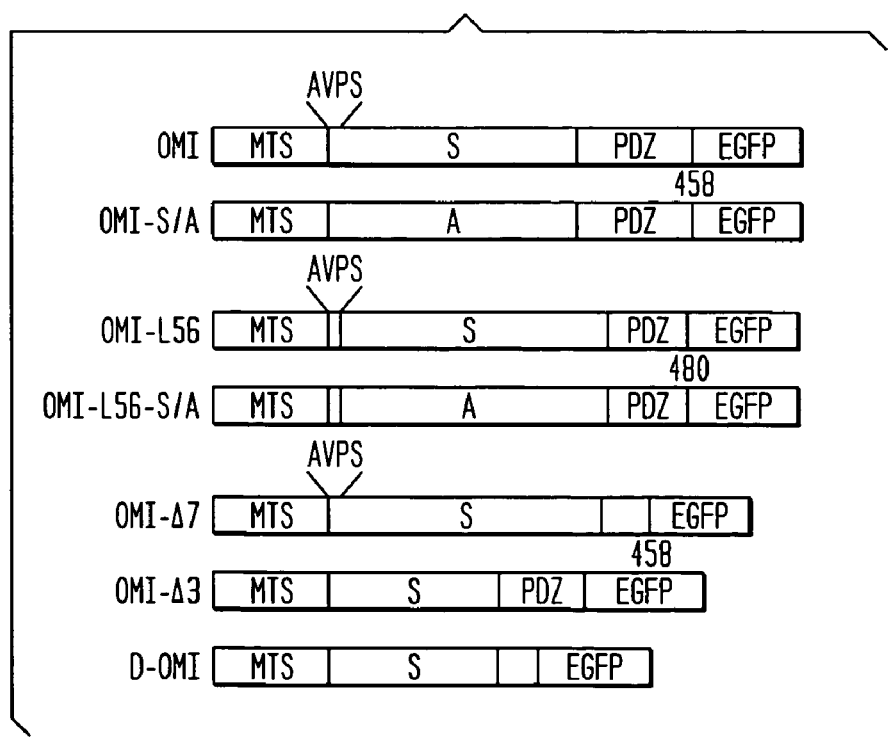
FIG. 13 is a schematic drawing showing the different Omi constructs.

To investigate the function of exon 3 that encodes part of the catalytic domain as well as exon 7 that encodes part of the PDZ domain, a number of chimeric proteins were made. A schematic diagram of these proteins is shown in FIG. 13. This list contains Omi/HtrA2 as well as D-Omi/HtrA2, Omi-Δ3 that lacks only the sequence encoded by exon 3 and Omi-Δ7 that lacks the sequence encoded by exon 7. Furthermore, several other constructs were made where the catalytic activity of Omi/HtrA2 was destroyed by an S/A substitution and an Omi/HtrA2 construct where both the catalytic and PDZ domains have been replaced with the corresponding domains of L56/HtrA2. For example, in Omi-SA, the Ser 306 (s) was replaced with Ala (A); Omi-L56 chimera is a construct where the N-terminus of Omi-HtrA2 including the AVPS motif was fused to L56 protein form the amino acid 156-480. Omi-L56-S/A is a mutated form of omi-L56, where the Ser 328 has been mutated to Ala. All of these constructs were cloned into EGFP-N1 vector. the conserved amino-terminal mitochondria targeting sequence (MTS) is shown, this is followed by the catalytic domain (which includes the AVPS motif), the catalytic domain if followed by the PDZ domain. All of these proteins were expressed as fusions with the green fluorescent protein (GFP). After transfection into mammalian cells, their localization, processing and ability to induce apoptosis was monitored.

Figure 14:
FIG. 14 is a photograph of an SDS-PAGE gel showing the expression and processing of the various Omi constructs.
Figure 15:
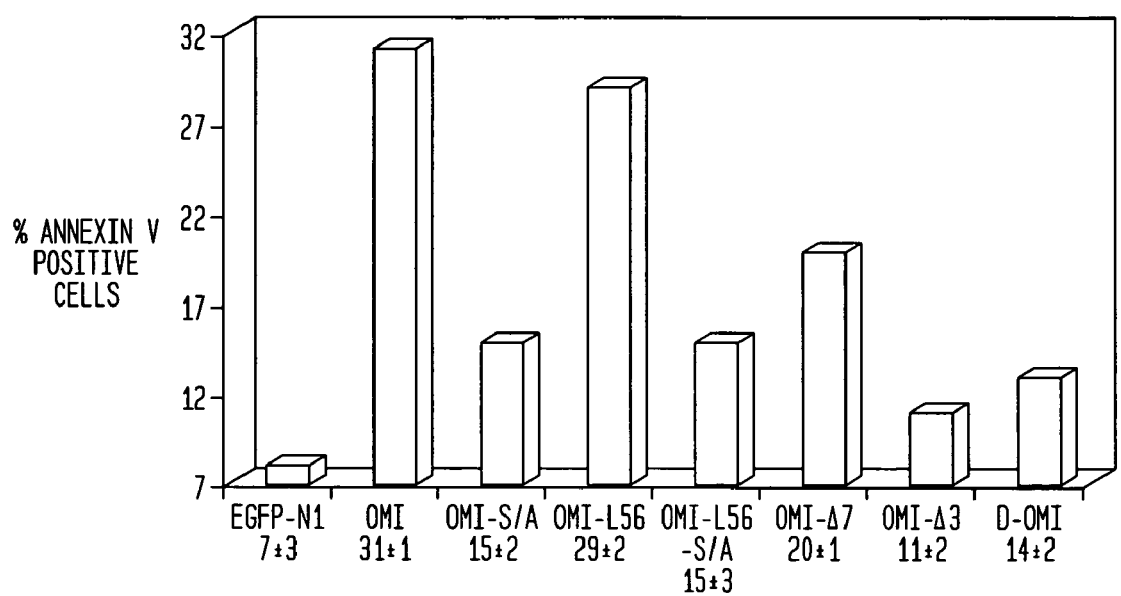
FIG. 15 is a bar graph showing the results of an apoptosis assay using the various Omi constructs.

FIG. 14 shows the expression and processing of the various GFP-fusion proteins. Equal amounts of whole-cell lysates obtained 24 hours post-transfection were subjected to SDS-PAGE followed by immunoblotting using anti-GFP antibodies. Lanes 1-7, cell lysates prepared from HeLa cells transfected with the corresponding construct: Omi-GFP, Omi-S/A-GFP, Omi-L56-GFP, Omi-L56-S/A-GFP, Omi-Δ7-GFP, Omi-Δ3-GFP, and D-Omi-GFP FIG. 15 shows the results from an apoptotic assay of various GFP-fusion proteins. 293T cells were transfected using the same constructs shown in FIG. 13. 48 hours later, transfected cells were detached and stained with PE-conjugated annexin V. The percentage of GFP positive cells that were also annexin V positive is shown. The number represents the average of four independent experiments.

This data shows that D-Omi, due to its inability to function as a protease, is not processed to the mature form of the protein. This causes the amino terminal part (aa 1-133) that is usually removed in the mature Omi/HtrA2 protein to remain attached on D-Omi. As a result, D-Omi is unable to induce apoptosis in a caspase-dependent manner since it can not expose the AVPS internal sequence motif necessary for binding to the inhibitor of apoptosis proteins (IAPs). Furthermore, since it is an inactive protease, it cannot induce apoptosis in a caspase-independent pathway. The results showed that D-Omi still retains some residual activity and it is able to induce apoptosis in 15% of transfected 293T cells, which is approximately half the apoptotic potential of mature Omi/HtrA2. The function of D-Omi is not known; it could act as a dominant negative, blocking the activity of Omi/HtrA2, or it could induce apoptosis in a new, independent mechanism.

Example 17

Kidney-Specific Substrates for Omi/HtrA2 Protease

This example describes the identification of substrates for Omi/HtrA2 protease. Omi/HtrA2 is an active serine protease. This activity is necessary for processing the precursor protein to its mature form. This processing exposes an internal AVPS motif at the amino terminus which is used to bind the inhibitor of apoptosis proteins (IAP) and induce caspase-dependent cell death. Furthermore, Omi/HtrA2 can induce apoptosis in a caspase-independent manner that relies entirely on its ability to function as a serine protease in the cytoplasm of cells. This observation suggests that the presence of specific substrates for Omi/HtrA2 whose destruction and removal is part of the caspase-independent apoptotic process. Alternatively, Omi/HtrA2 might activate a precursor pro-apoptotic protein through limited proteolytic cleavage.

In order to identify substrates for Omi/HtrA2, the latest technology in proteomics was used. Human kidney extracts obtained from BioChain Institute, Inc. (Hayward, Calif.). These extracts were already fractionated into: (a) kidney membrane associated proteins and (b) kidney cytoplasmic proteins. About 200 mg of extract was incubated in the presence of bacterially made His-Omi-134-458. As controls, no enzyme was added nor was the ucf-101 inhibitor used. After 30 min of incubation at 37° C., the reaction was stopped with an equal amount of SDS-PAGE buffer. Proteins were analyzed by 2-dimensional gel electrophoresis. This service was done in Kendrick's lab (Madison, Wis.). This lab specializes in 2D PAGE and provides a service for academia (http://www.kendricklabs.com/). When the images of the 2D-gels were compared, two polypeptides (32 kD and 29 kD) in the human kidney cytoplasmic fraction were specifically cleaved by His-Omi (results not shown). This cleavage was prevented by the specific inhibitor ucf-101. It was also not seen when the enzyme was left out of the reaction. No proteins were cleaved in the membrane bound fractions. After scaling-up the reaction, the two polypeptide spots were excised and sent to the Protein Chemistry Core Facility, Howard Hughes Medical Institute/Columbia University for mass spectrometry sequencing.

There, the proteins were identified as 14-3-3 protein and annexin V. 14-3-3 proteins are small acidic proteins with molecular mass ranging from 27 to 32 kDa with no detectable catalytic domain or function (Aitken, et al. (1995) *Biochem Soc Trans*, 23, 605-11; Dubois, et al. (1997) *J Protein Chem*, 16, 513-22; Muslin, et al. (2000) *Cell Signal*, 12, 703-9; Shaw, (2000), *Curr Biol*, 10, R400; and Skoulakis, et al. (1998) *Mol Neurobiol*, 16, 269-84. 1998).

There are seven identified 14-3-3 isoforms in mammals and these are highly conserved through evolution from the yeast to mammals. 14-3-3 proteins are phosphoserine-binding proteins involved in cellular proliferation, checkpoint control and apoptosis (Aitken, et al. (1995) supra). The mode of action of 14-3-3 proteins is not due to any intrinsic activity. Instead, it relies entirely on the ability of 14-3-3 proteins to bind specific targets and modify their activity. For instance, 14-3-3 binding to BAD competes with Bcl2 binding, relieving Bcl2 for its antiapoptotic function (Datta, et al. (2000) *Mol Cell*, 6, 41-51). 14-3-3 proteins can also modify the target protein localization (Muslin, et al. (2000) *Cell Signal*, 12, 703-9), bridge two proteins together (Luo, et al. (1996) *Nature*, 383, 181-5), alter the catalytic activity of the target protein, or they can protect the target protein from modifications such as dephosphorylation (Chiang, et al. (2001) *Blood*, 97, 1289-97). Approximately 70 target polypeptides for 14-3-3 proteins have been identified so far (Tzivion, et al. (2000) *J. Biol Chem*, 275, 29772-8). If 14-3-3 proteins are indeed physiological substrates for Omi/HtrA2, it will help to explain how Omi/HtrA2 causes caspase-independent cell death. It has been reported that when the 14-3-35 protein (one of the seven 14-3-3 isoforms) was disrupted in a human colorectal cancer cell line, cells arrested in the G2 phase and ultimately perished by non-apoptotic cell death (Chan, et al. (1999) *Nature*, 401, 616-20).

Annexin V is a vascular anticoagulant protein that is normally present on the cytosolic site of the plasma membrane (Tait, et al. (1988) *Biochemistry*, 27, 6268-76; and Reutelingsperger, et al. (1988) *Eur J. Biochem*, 173, 171-8). Annexin V is a member of the calcium dependent phospholipid binding annexin/lipocortin protein family. It is composed of 320 amino acid residues folded into a planar cyclical arrangement of four 70-amino acid repeats (Huber, et al. (1992) *Behring Inst Mitt*, 107-25). Most cells and tissues express annexin V (Kaetzel, et al. (1989) *Biochem Biophys Res Commun*, 160, 1233-7). Some known activities of annexin V include collagen binding (Pfaffle, et al. (1988) *EMBO J*, 7, 2335-42), formation of voltage dependent calcium channels (Rojas, et al. (1990) *J. Biol Chem*, 265, 21207-15) and inhibition of phospholipase A2 (Pepinsky, et al. (1988) *J. Biol Chem*, 263, 10799-811) and protein kinase C (Schlaepfer, et al. (1992) *Biochemistry*, 31, 1886-91). The high affinity of annexin V for phospholipids has been exploited as a measure of apoptosis in a variety of cell types. Early apoptosis is characterized by exposure of phospholipids to the matrix side of the membrane (Fadok, et al. (1992) *J Immunol*, 148, 2207-16). Fluorescent-labeled annexin V binding to the newly exposed phospholipids is used to identify and quantitate apoptotic cells (Koopman, et al. (1994) *Blood*, 84, 1415-20; and Vermes, et al. (1995) *J Immunol Methods*, 184, 39-51).

These data show that both 14-3-3 and Annexin V are cleared by Omi/HtrA2 and are physiological substrates of Omi/HtrA2.

What is claimed is:

1. A method of inhibiting Omi/HtrA2 activity, from about 20% to about 90% comprising:
   contacting a cell having Omi/HtrA2 activity with an apoptosis inhibiting compound; and
   monitoring the inhibition of Omi/HtrA2 activity, wherein the apoptosis inhibiting compound is selected from the group consisting of:

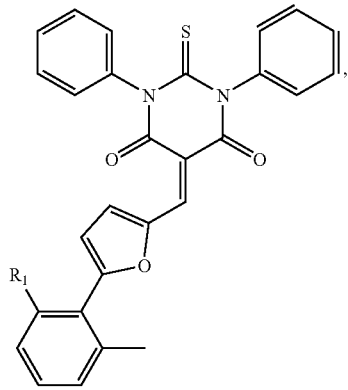
(I)

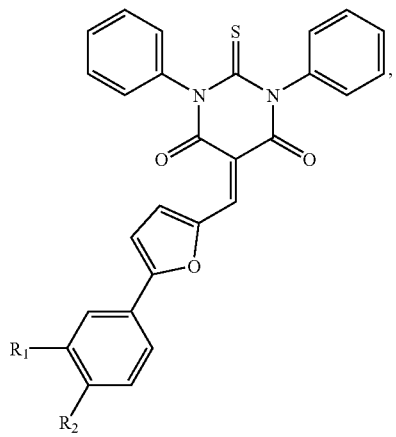
(II)

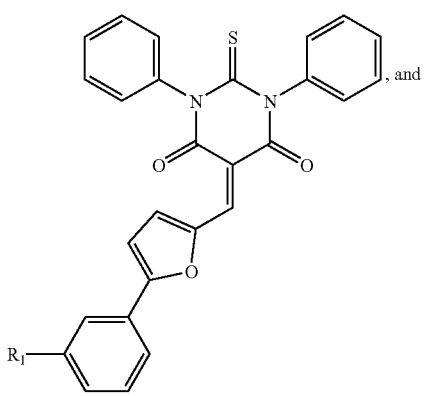
(III)

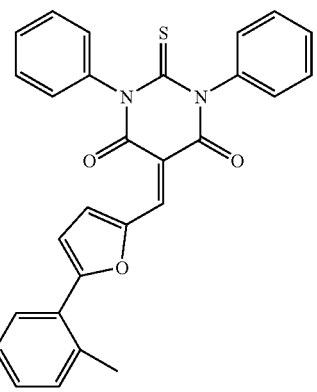
(IV)

where $R_1$ is selected from the group consisting of a chloride, nitro group, a carboxy group, a hydroxide, an aliphatic group, an aromatic group, an acyl group, an alkoxy group, an alkylene group, an alkenylene group, an alkynylene group, a hydroxycarbonylalkyl group, an anhydride, an amide, an amine, and a heterocyclic aromatic group, and where $R_2$ is a methoxy group.

2. The method of claim 1, wherein the step of contacting the cell comprises contacting the cell in vivo.

3. The method of claim 1, wherein the step of contacting the cell comprises contacting the cell in vitro.

4. The method of claim 1, wherein the apoptosis inhibiting compound is formula I, wherein $R_1$ is a nitro group (ucf-101).

5. The method of claim 1, wherein the apoptosis inhibiting compound is formula II, wherein $R_1$ is a chloride and $R_2$ is a methoxy group (ucf-102).

6. The method of claim 1, wherein the apoptosis inhibiting compound is formula III, wherein $R_1$ is $CO_2H$ (ucf-103).

7. The method of claim 1, wherein the apoptosis inhibiting compound is formula IV, wherein $R_1$ is a nitro group (ucf-104).

8. The method of claim 1, wherein the step of monitoring Omi/HtrA2 activity comprises monitoring a change in fluorescene of an Omi/HtrA2 substrate coupled to a fluorescent marker.

9. The method of claim 1, wherein the step of monitoring the inhibition of Omi/HtrA2 activity further comprises monitoring apoptosis of the cell.

10. The method of claim 8, wherein the fluorescent marker is selected from the group consisting of fluorescein isothiocyanate (FITC), cyanine dye-5 (CYS), cyanine dye-3 (Cy3), cyanine dye-7 (Cy7), allophycocyanin (APC), tetramethyl rhodamine isothiocyanate (TRITC), and phycoerythrin (PE).

11. A method of inhibiting Omi/HtrA2 activity, comprising:
    contacting a cell having Omi/HtrA2 activity with an apoptosis inhibiting compound; and
    monitoring the inhibition of Omi/HtrA2 activity,
    wherein the apoptosis inhibiting compound is selected from the group consisting of Ucf-101 Ucf-102, Ucf-103 and Ucf-104.

12. A method for inhibiting caspase-independent apoptosis in a cell comprising:
    contacting a cell having Omi/HtrA2 activity with at least one apoptosis inhibiting compound selected from the group consisting of Ucf-101 Ucf-102, Ucf-103 and Ucf-104, such that the apoptosis inhibiting compound interacts with Omi/HtrA2 to inhibit the activity of Omi/HtrA2, wherein the inhibition of Omi/HtrA2 activity reduces apoptosis in the cell; and monitoring the inhibition of apoptosis.

* * * * *

UNITED STATES PATENT AND TRADEMARK OFFICE
CERTIFICATE OF CORRECTION

| | | Page 1 of 1 |
|---|---|---|
| PATENT NO. | : 7,713,981 B2 | |
| APPLICATION NO. | : 10/728056 | |
| DATED | : May 11, 2010 | |
| INVENTOR(S) | : Antonis Zervos | |

It is certified that error appears in the above-identified patent and that said Letters Patent is hereby corrected as shown below:

In the Specifications:

Please add in column 1, at line 11, the following paragraph:

-- Statement Regarding Federally Sponsored Research or Development
This invention was made with government support under R01 DK055734 awarded by the National Institutes of Health. The government has certain rights in the invention. --

Signed and Sealed this
Twenty-eighth Day of January, 2014

Michelle K. Lee
*Deputy Director of the United States Patent and Trademark Office*